US011318470B2

(12) United States Patent
Culbertson et al.

(10) Patent No.: US 11,318,470 B2
(45) Date of Patent: May 3, 2022

(54) MICROFLUIDICS-BASED NANOBIOSENSORS AND DEVICES

(71) Applicant: Kansas State University Research Foundation, Manhattan, KS (US)

(72) Inventors: Christopher T. Culbertson, Manhattan, KS (US); Stefan H. Bossmann, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 462 days.

(21) Appl. No.: 16/349,700

(22) PCT Filed: Nov. 17, 2017

(86) PCT No.: PCT/US2017/062304
§ 371 (c)(1),
(2) Date: May 14, 2019

(87) PCT Pub. No.: WO2018/094213
PCT Pub. Date: May 24, 2018

(65) Prior Publication Data
US 2019/0351416 A1 Nov. 21, 2019

Related U.S. Application Data

(60) Provisional application No. 62/455,853, filed on Feb. 7, 2017, provisional application No. 62/424,224, filed on Nov. 18, 2016.

(51) Int. Cl.
B81B 5/00 (2006.01)
B01L 3/00 (2006.01)
(Continued)

(52) U.S. Cl.
CPC ..... B01L 3/502761 (2013.01); B01L 3/50273 (2013.01); C07K 1/22 (2013.01);
(Continued)

(58) Field of Classification Search
None
See application file for complete search history.

(56) References Cited

U.S. PATENT DOCUMENTS 8,969,027 B2 3/2015 Bossmann et al.
9,216,154 B2 12/2015 Bossmann et al.
(Continued)

FOREIGN PATENT DOCUMENTS

WO 2016149637 9/2016

OTHER PUBLICATIONS

International Search Report and Written Opinion in corresponding PCT/US2017/062304, dated Mar. 27, 2018.

*Primary Examiner* — Paul S Hyun
(74) *Attorney, Agent, or Firm* — Hovey Williams LLP

(57) ABSTRACT

Microfluidic devices and nanobiosensors comprising a magnetic nanoparticle attached to a reporter molecule via a release unit for microfluidic-based detection of a target analyte in a biological sample. The nanobiosensors can be magnetically manipulated or guided through the microfluidics channels for incubation with the biological sample, concentration of the nanobiosensors, and detection of target analytes, without having to pump the entire initial sample through a microfluidic channel of the microfluidic device. The magnetic nanoparticles are separated from the reporter molecules before detection and can be re-used.

17 Claims, 10 Drawing Sheets

Specification includes a Sequence Listing.

(51) Int. Cl.
     *C07K 1/22*     (2006.01)
     *C07K 1/28*     (2006.01)
     *G01N 1/30*     (2006.01)
     *G01N 1/34*     (2006.01)
     *G01N 1/38*     (2006.01)
     *B82Y 30/00*     (2011.01)

(52) U.S. Cl.
     CPC ................ *C07K 1/28* (2013.01); *G01N 1/30* (2013.01); *G01N 1/34* (2013.01); *G01N 1/38* (2013.01); *B01L 2200/0647* (2013.01); *B01L 2400/043* (2013.01); *B82Y 30/00* (2013.01); *G01N 2001/388* (2013.01)

(56) References Cited

U.S. PATENT DOCUMENTS

| | | |
|---|---|---|
| 2006/0054504 A1 | 3/2006 | Lee et al. |
| 2007/0054337 A1 | 3/2007 | Ferning et al. |
| 2009/0136582 A1* | 5/2009 | Albrecht ................ A61P 43/00 424/490 |
| 2012/0071330 A1* | 3/2012 | Kokoris ............... C12Q 1/6832 506/4 |
| 2014/0030717 A1 | 1/2014 | Zhong et al. |
| 2015/0290639 A1 | 10/2015 | Evtodienko |
| 2015/0357102 A1 | 12/2015 | Rowe et al. |
| 2017/0219548 A1 | 8/2017 | Troyer et al. |

* cited by examiner

SEQUENCE LISTING

<160> NUMBER OF SEQ ID NOS: 108

<210> SEQ ID NO 1
<211> LENGTH: 7
<212> TYPE: PRT
<213> ORGANISM: Artificial Sequence
<220> FEATURE:
<223> OTHER INFORMATION: Synthetic supramolecular recognition sequence

<400> SEQUENCE: 1

Cys Gln Glu Gln Phe Trp Trp
1               5

<210> SEQ ID NO 2
<211> LENGTH: 13
<212> TYPE: PRT
<213> ORGANISM: Artificial Sequence
<220> FEATURE:
<223> OTHER INFORMATION: Synthetic supramolecular recognition sequence

<400> SEQUENCE: 2

Pro Tyr Phe Pro Arg Gly Ser Ser Tyr Gln Gly Trp Asn
1               5                   10

<210> SEQ ID NO 3
<211> LENGTH: 6
<212> TYPE: PRT
<213> ORGANISM: Artificial Sequence
<220> FEATURE:
<223> OTHER INFORMATION: Synthetic supramolecular recognition sequence

<400> SEQUENCE: 3

Cys Cys Ile Gln Asn Gln
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic supramolecular recognition sequence

<400> SEQUENCE: 4

Ala Trp Tyr Gln Pro Gln Phe Glu
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic supramolecular recognition sequence

<400> SEQUENCE: 5

Glu Gln Gln Lys Arg Asn
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic supramolecular recognition sequence

<400> SEQUENCE: 6

Cys Asn His Gly Lys Phe Tyr Cys
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic supramolecular recognition sequence

<400> SEQUENCE: 7

Asn Ile Tyr Cys Asn Ile Ala Tyr
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic supramolecular recognition sequence

<400> SEQUENCE: 8

Lys Ala Tyr Arg Trp Glu Phe Ile
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic supramolecular recognition sequence

<400> SEQUENCE: 9

Ile Gln Asn Ser Gly Ala Pro Cys His
1               5

<210> SEQ ID NO 10
<211> LENGTH: 10
<212> TYPE: PRT
<213> ORGANISM: Artificial Sequence
<220> FEATURE:
<223> OTHER INFORMATION: Synthetic supramolecular recognition sequence

<400> SEQUENCE: 10

Trp Gln Glu Ala Lys Asn Ala Asn Gln Met
1               5                   10

<210> SEQ ID NO 11
<211> LENGTH: 8
<212> TYPE: PRT
<213> ORGANISM: Artificial Sequence
<220> FEATURE:
<223> OTHER INFORMATION: Synthetic supramolecular recognition sequence

<400> SEQUENCE: 11

Arg His Gln Lys Thr Tyr Ser Phe
1               5

<210> SEQ ID NO 12
<211> LENGTH: 10
<212> TYPE: PRT
<213> ORGANISM: Artificial Sequence
<220> FEATURE:
<223> OTHER INFORMATION: Synthetic supramolecular recognition sequence
<220> FEATURE:
<221> NAME/KEY: misc_feature
<222> LOCATION: (1)..(1)
<223> OTHER INFORMATION: Xaa can be any naturally occurring amino acid

<400> SEQUENCE: 12

```
Xaa Leu Pro Pro His Trp Ala Gly Ala Leu
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic supramolecular recognition sequence
<220> FEATURE:
<221> NAME/KEY: misc_feature
<222> LOCATION: (1)..(1)
<223> OTHER INFORMATION: Xaa can be any naturally occurring amino acid

<400> SEQUENCE: 13

Xaa Leu Pro Pro His Trp Ala Phe Ala Leu
1               5                   10

<210> SEQ ID NO 14
<211> LENGTH: 28
<212> TYPE: PRT
<213> ORGANISM: Artificial Sequence
<220> FEATURE:
<223> OTHER INFORMATION: Synthetic supramolecular recognition sequence

<400> SEQUENCE: 14

Leu Thr Glu Leu Glu Lys Ala Leu Asn Ser Ile Ile Asp Val Tyr His
1               5                   10                  15

Lys Tyr Ser Leu Ile Lys Gly Asn Phe His Ala Val
            20                  25

<210> SEQ ID NO 15
<211> LENGTH: 30
<212> TYPE: PRT
<213> ORGANISM: Artificial Sequence
<220> FEATURE:
<223> OTHER INFORMATION: Synthetic supramolecular recognition sequence

<400> SEQUENCE: 15

Gly Glu Ser Met Asn Phe Ser Asp Val Phe Asp Ser Ser Glu Asp Tyr
1               5                   10                  15

Phe Val Ser Val Asn Thr Ser Tyr Tyr Ser Val Asp Ser Glu
            20                  25                  30

<210> SEQ ID NO 16
<211> LENGTH: 12
<212> TYPE: PRT
<213> ORGANISM: Artificial Sequence
<220> FEATURE:
<223> OTHER INFORMATION: Synthetic supramolecular recognition sequence

<400> SEQUENCE: 16

Gly Thr Gln Trp Trp Val Val Cys Gln Gln Phe Gly
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic supramolecular recognition sequence

<400> SEQUENCE: 17

Pro Gly His Trp Ser Asp Trp Ser Pro Ser
1               5                   10
```

<210> SEQ ID NO 18
<211> LENGTH: 28
<212> TYPE: PRT
<213> ORGANISM: Artificial Sequence
<220> FEATURE:
<223> OTHER INFORMATION: Synthetic supramolecular recognition sequence

<400> SEQUENCE: 18

Tyr Phe Pro Glu Pro Val Thr Val Ser Gly Ala Gly Thr Phe Pro Ala
1               5                   10                  15

Val Leu Gly Ser Gly Gln Pro Pro Gly Lys Gly Leu
            20                  25

<210> SEQ ID NO 19
<211> LENGTH: 25
<212> TYPE: PRT
<213> ORGANISM: Artificial Sequence
<220> FEATURE:
<223> OTHER INFORMATION: Synthetic supramolecular recognition sequence

<400> SEQUENCE: 19

Thr Ala Val Tyr Tyr Cys Ala Asn Arg Ala Gly Trp Gly Met Gly Asp
1               5                   10                  15

Tyr Trp Gly Gln Gly Thr Gln Val Thr
            20                  25

<210> SEQ ID NO 20
<211> LENGTH: 16
<212> TYPE: PRT
<213> ORGANISM: Artificial Sequence
<220> FEATURE:
<223> OTHER INFORMATION: Synthetic supramolecular recognition sequence

<400> SEQUENCE: 20

Thr Ala Ser Asn Tyr Gly Ala Gly Tyr Ser Thr Asn Asp Arg His Ser
1               5                   10                  15

<210> SEQ ID NO 21
<211> LENGTH: 10
<212> TYPE: PRT
<213> ORGANISM: Artificial Sequence
<220> FEATURE:
<223> OTHER INFORMATION: Synthetic supramolecular recognition sequence

<400> SEQUENCE: 21

Asn Arg Pro Ala Gln Ala Trp Met Leu Gly
1               5                   10

<210> SEQ ID NO 22
<211> LENGTH: 20
<212> TYPE: PRT
<213> ORGANISM: Artificial Sequence
<220> FEATURE:
<223> OTHER INFORMATION: Synthetic supramolecular recognition sequence

<400> SEQUENCE: 22

Ala Val Tyr Tyr Cys Gln Gln Asn Asn Glu Asp Pro Arg Thr Phe Gly
1               5                   10                  15

Gly Gly Thr Lys
            20

<210> SEQ ID NO 23
<211> LENGTH: 13
<212> TYPE: PRT
<213> ORGANISM: Artificial Sequence

```
<220> FEATURE:
<223> OTHER INFORMATION: Synthetic supramolecular recognition sequence

<400> SEQUENCE: 23

Ala Gly Asp Gly Tyr Tyr Pro Tyr Ala Met Asp Asn Trp
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Synthetic supramolecular recognition sequence

<400> SEQUENCE: 24

Gly Trp Leu Pro Phe Gly Phe Ile Leu Ile Ser Ala Gly
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Synthetic supramolecular recognition sequence

<400> SEQUENCE: 25

Tyr Gln Gln Lys Pro Gly Gln Pro Pro Lys Leu
1               5                   10

<210> SEQ ID NO 26
<211> LENGTH: 29
<212> TYPE: PRT
<213> ORGANISM: Artificial Sequence
<220> FEATURE:
<223> OTHER INFORMATION: Synthetic supramolecular recognition sequence

<400> SEQUENCE: 26

Ser Val Asn Trp Ile Arg Gln Pro Pro Gly Lys Ala Leu Glu Trp Leu
1               5                   10                  15

Ala Met Ile Trp Gly Asp Gly Lys Ile Val Tyr Asn Ser
            20                  25

<210> SEQ ID NO 27
<211> LENGTH: 10
<212> TYPE: PRT
<213> ORGANISM: Artificial Sequence
<220> FEATURE:
<223> OTHER INFORMATION: Synthetic supramolecular recognition sequence

<400> SEQUENCE: 27

Trp Leu Pro Phe Gly Phe Ile Leu Ile Ser
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Synthetic supramolecular recognition sequence

<400> SEQUENCE: 28

Thr Tyr Tyr Cys Gln Gln Trp Ser Gly Tyr Pro Tyr Thr Phe
1               5                   10

<210> SEQ ID NO 29
<211> LENGTH: 13
```

```
<212> TYPE: PRT
<213> ORGANISM: Artificial Sequence
<220> FEATURE:
<223> OTHER INFORMATION: Synthetic supramolecular recognition sequence

<400> SEQUENCE: 29

Ser His Phe Pro Tyr Ser Gln Tyr Gln Phe Trp Lys Asn
1               5                   10

<210> SEQ ID NO 30
<211> LENGTH: 35
<212> TYPE: PRT
<213> ORGANISM: Artificial Sequence
<220> FEATURE:
<223> OTHER INFORMATION: Synthetic supramolecular recognition sequence

<400> SEQUENCE: 30

Asp Met Ser Asp Thr Asn Trp Trp Lys Gly Thr Ser Lys Gly Arg Thr
1               5                   10                  15

Gly Leu Ile Pro Ser Asn Tyr Val Ala Glu Gln Ala Glu Ser Ile Asp
            20                  25                  30

Asn Pro Leu
        35

<210> SEQ ID NO 31
<211> LENGTH: 17
<212> TYPE: PRT
<213> ORGANISM: Artificial Sequence
<220> FEATURE:
<223> OTHER INFORMATION: Synthetic supramolecular recognition sequence

<400> SEQUENCE: 31

Ile Ala Gly Lys Leu Gln Ser Ala Gly Ser Ala Leu Trp Thr Asp Gln
1               5                   10                  15

Leu

<210> SEQ ID NO 32
<211> LENGTH: 19
<212> TYPE: PRT
<213> ORGANISM: Artificial Sequence
<220> FEATURE:
<223> OTHER INFORMATION: Synthetic supramolecular recognition sequence

<400> SEQUENCE: 32

Ser Ser Pro Lys His Val Arg Phe Ser Trp His Gln Asp Ala Val Thr
1               5                   10                  15

Val Thr Cys

<210> SEQ ID NO 33
<211> LENGTH: 10
<212> TYPE: PRT
<213> ORGANISM: Artificial Sequence
<220> FEATURE:
<223> OTHER INFORMATION: Synthetic supramolecular recognition sequence

<400> SEQUENCE: 33

Ala Lys Cys Cys Pro Cys Gln Gln Trp Trp
1               5                   10

<210> SEQ ID NO 34
<211> LENGTH: 8
<212> TYPE: PRT
<213> ORGANISM: Artificial Sequence
<220> FEATURE:
<223> OTHER INFORMATION: Synthetic protease consensus sequence
```

```
<400> SEQUENCE: 34

Leu Ala Gln Ala Val Val Ser Ser
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 35

Gly Ser Gln His Ile Arg Ala Glu
1               5

<210> SEQ ID NO 36
<211> LENGTH: 12
<212> TYPE: PRT
<213> ORGANISM: Artificial Sequence
<220> FEATURE:
<223> OTHER INFORMATION: Synthetic protease consensus sequence

<400> SEQUENCE: 36

Ser Leu Leu Lys Ser Arg Met Val Pro Asn Phe Asn
1               5                   10

<210> SEQ ID NO 37
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 37

Gly Asp Ser Gly Leu Gly Arg Ala
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 38

Glu Val Ala Leu Val Ala Leu Lys
1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 39

Leu Gly Leu Glu Gly Ala Asn Leu
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic protease consensus sequence
```

```
<400> SEQUENCE: 40

Ala Ala Leu Gly Ser Ala Pro Gly
1               5

<210> SEQ ID NO 41
<211> LENGTH: 12
<212> TYPE: PRT
<213> ORGANISM: Artificial Sequence
<220> FEATURE:
<223> OTHER INFORMATION: Synthetic protease consensus sequence

<400> SEQUENCE: 41

Ser Leu Leu Ile Phe Arg Ser Trp Ala Asn Phe Asn
1               5                   10

<210> SEQ ID NO 42
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 42

Val Glu Pro Asn Ser Leu Glu Glu
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 43

Gly Glu Pro Leu Ser Leu Leu Pro
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 44

Ile Pro Val Ser Leu Arg Ser Gly
1               5

<210> SEQ ID NO 45
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 45

Arg Pro Phe Ser Met Ile Met Gly
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 46
```

Val Pro Leu Ser Leu Thr Met Gly
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 47

Gly Pro Ser Gly Leu Arg Gly Ala
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 48

Val Pro Leu Ser Leu Tyr Ser Gly
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 49

Gly Ala Ala Asn Leu Val Arg Gly
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic protease consensus sequence

<400> SEQUENCE: 50

Gly Val Pro Leu Ser Leu Thr Met Gly
1               5

<210> SEQ ID NO 51
<211> LENGTH: 11
<212> TYPE: PRT
<213> ORGANISM: Artificial Sequence
<220> FEATURE:
<223> OTHER INFORMATION: Synthetic protease consensus sequence

<400> SEQUENCE: 51

Pro Gln Gly Leu Ala Gly Gln Arg Gly Ile Val
1               5                   10

<210> SEQ ID NO 52
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 52

Gly Pro Ala Gly Leu Arg Leu Ala
1               5

<210> SEQ ID NO 53
<211> LENGTH: 11
<212> TYPE: PRT
<213> ORGANISM: Artificial Sequence
<220> FEATURE:
<223> OTHER INFORMATION: Synthetic enzyme consensus sequence

<400> SEQUENCE: 53

Arg Asp Ile Tyr Ala Ala Pro Phe Phe Arg Lys
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Synthetic enzyme consensus sequence

<400> SEQUENCE: 54

Ala Met Glu Arg Arg Arg Thr Ser Ala Ala Arg Arg Ser Tyr
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Synthetic enzyme consensus sequence

<400> SEQUENCE: 55

Lys Ala Arg Ala Ala Val Ser Pro Gln Lys Arg Lys Ala
1               5                   10

<210> SEQ ID NO 56
<211> LENGTH: 16
<212> TYPE: PRT
<213> ORGANISM: Artificial Sequence
<220> FEATURE:
<223> OTHER INFORMATION: Synthetic enzyme consensus sequence

<400> SEQUENCE: 56

Arg Ala Arg Lys Arg Arg Leu Ser Ala Pro Pro Leu Ala Ser Gly Asp
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Synthetic enzyme consensus sequence

<400> SEQUENCE: 57

Ala Lys Ala Gly Pro Pro Leu Ser Pro Arg Pro Pro His Val His
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Synthetic enzyme consensus sequence

<400> SEQUENCE: 58

Asp Leu Phe Ile Pro Asp Asn Tyr Leu Lys Met Lys Pro Ala Pro

```
<210> SEQ ID NO 59
<211> LENGTH: 15
<212> TYPE: PRT
<213> ORGANISM: Artificial Sequence
<220> FEATURE:
<223> OTHER INFORMATION: Synthetic enzyme consensus sequence

<400> SEQUENCE: 59

Ala Glu Leu Asp Pro Glu Asp Ser Met Asp Met Asp Met Ala Pro
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Synthetic enzyme consensus sequence

<400> SEQUENCE: 60

Glu Asp Glu Ala Glu Glu Leu Ser Asp Glu Asp Glu Glu Leu Lys
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Synthetic enzyme consensus sequence

<400> SEQUENCE: 61

Ala Ala Gly Pro Ala Pro Leu Ser Pro Val Pro Pro Val Val His
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Synthetic enzyme consensus sequence

<400> SEQUENCE: 62

Asp Ala Ser Arg Pro Pro Pro Leu Ser Pro Leu Pro Ser Pro Arg Ala
1               5                   10                  15

<210> SEQ ID NO 63
<211> LENGTH: 9
<212> TYPE: PRT
<213> ORGANISM: Artificial Sequence
<220> FEATURE:
<223> OTHER INFORMATION: Synthetic enzyme consensus sequence

<400> SEQUENCE: 63

Gly Arg Arg Arg Arg Arg Arg Arg Gly
1               5

<210> SEQ ID NO 64
<211> LENGTH: 5
<212> TYPE: PRT
<213> ORGANISM: Artificial Sequence
<220> FEATURE:
<223> OTHER INFORMATION: Synthetic protease consensus sequence

<400> SEQUENCE: 64

Ser Gly Arg Ser Ala
1               5
```

<210> SEQ ID NO 65
<211> LENGTH: 13
<212> TYPE: PRT
<213> ORGANISM: Artificial Sequence
<220> FEATURE:
<223> OTHER INFORMATION: Synthetic reporter molecule sequence

<400> SEQUENCE: 65

Ala Arg Asp Ile Tyr Ala Ala Pro Phe Phe Arg Lys Cys
1               5                   10

<210> SEQ ID NO 66
<211> LENGTH: 17
<212> TYPE: PRT
<213> ORGANISM: Artificial Sequence
<220> FEATURE:
<223> OTHER INFORMATION: Synthetic reporter molecule sequence

<400> SEQUENCE: 66

Asp Asp Ala Met Glu Arg Arg Arg Thr Ser Ala Ala Arg Arg Ser Tyr
1               5                   10                  15

Cys

<210> SEQ ID NO 67
<211> LENGTH: 18
<212> TYPE: PRT
<213> ORGANISM: Artificial Sequence
<220> FEATURE:
<223> OTHER INFORMATION: Synthetic reporter molecule sequence

<400> SEQUENCE: 67

Ile Cys Lys Ala Arg Ala Ala Val Ser Pro Gln Lys Arg Lys Ala Asp
1               5                   10                  15

Asp Cys

<210> SEQ ID NO 68
<211> LENGTH: 20
<212> TYPE: PRT
<213> ORGANISM: Artificial Sequence
<220> FEATURE:
<223> OTHER INFORMATION: Synthetic reporter molecule sequence

<400> SEQUENCE: 68

Asp Asp Cys Arg Ala Arg Lys Arg Arg Leu Ser Ala Pro Pro Leu Ala
1               5                   10                  15

Ser Gly Asp Cys
            20

<210> SEQ ID NO 69
<211> LENGTH: 16
<212> TYPE: PRT
<213> ORGANISM: Artificial Sequence
<220> FEATURE:
<223> OTHER INFORMATION: Synthetic reporter molecule sequence

<400> SEQUENCE: 69

Ala Lys Ala Gly Pro Pro Leu Ser Pro Arg Pro Pro His Val His Cys
1               5                   10                  15

<210> SEQ ID NO 70
<211> LENGTH: 16
<212> TYPE: PRT
<213> ORGANISM: Artificial Sequence
<220> FEATURE:

```
<223> OTHER INFORMATION: Synthetic reporter molecule sequence

<400> SEQUENCE: 70

Asp Leu Phe Ile Pro Asp Asn Tyr Leu Lys Met Lys Pro Ala Pro Cys
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: Synthetic reporter molecule sequence

<400> SEQUENCE: 71

Ala Glu Leu Asp Pro Glu Asp Ser Met Asp Met Asp Met Ala Pro Cys
1               5                   10                  15

<210> SEQ ID NO 72
<211> LENGTH: 16
<212> TYPE: PRT
<213> ORGANISM: Artificial Sequence
<220> FEATURE:
<223> OTHER INFORMATION: Synthetic reporter molecule sequence

<400> SEQUENCE: 72

Glu Asp Glu Ala Glu Glu Leu Ser Asp Glu Asp Glu Glu Leu Lys Cys
1               5                   10                  15

<210> SEQ ID NO 73
<211> LENGTH: 16
<212> TYPE: PRT
<213> ORGANISM: Artificial Sequence
<220> FEATURE:
<223> OTHER INFORMATION: Synthetic reporter molecule sequence

<400> SEQUENCE: 73

Ala Ala Gly Pro Ala Pro Leu Ser Pro Val Pro Pro Val Val His Cys
1               5                   10                  15

<210> SEQ ID NO 74
<211> LENGTH: 17
<212> TYPE: PRT
<213> ORGANISM: Artificial Sequence
<220> FEATURE:
<223> OTHER INFORMATION: Synthetic reporter molecule sequence

<400> SEQUENCE: 74

Asp Ala Ser Arg Pro Pro Pro Leu Ser Pro Leu Pro Ser Pro Arg Ala
1               5                   10                  15

Cys

<210> SEQ ID NO 75
<211> LENGTH: 17
<212> TYPE: PRT
<213> ORGANISM: Artificial Sequence
<220> FEATURE:
<223> OTHER INFORMATION: Synthetic reporter molecule sequence

<400> SEQUENCE: 75

Gly Ala Gly Cys Asp Ser Asp Gly Pro Glu Gly Leu Arg Gly Ala Arg
1               5                   10                  15

Gly

<210> SEQ ID NO 76
<211> LENGTH: 19
```

```
<212> TYPE: PRT
<213> ORGANISM: Artificial Sequence
<220> FEATURE:
<223> OTHER INFORMATION: Synthetic reporter molecule sequence

<400> SEQUENCE: 76

His His His His His His Cys Gly Pro Glu Gly Leu Arg Gly Ala Glu
1               5                   10                  15

Glu Glu Glu

<210> SEQ ID NO 77
<211> LENGTH: 11
<212> TYPE: PRT
<213> ORGANISM: Artificial Sequence
<220> FEATURE:
<223> OTHER INFORMATION: Synthetic reporter molecule sequence

<400> SEQUENCE: 77

His His His His His His Cys Gly Pro Glu Gly
1               5                   10

<210> SEQ ID NO 78
<211> LENGTH: 14
<212> TYPE: PRT
<213> ORGANISM: Artificial Sequence
<220> FEATURE:
<223> OTHER INFORMATION: Synthetic reporter molecule sequence

<400> SEQUENCE: 78

His Gly Ala Gly Cys Gly Pro Ser Ala Leu Val Ser Asp Gly
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Synthetic reporter molecule sequence

<400> SEQUENCE: 79

His Gly Ala Gly Cys Gly Pro Ala Gly Leu Arg Gly Leu Gly
1               5                   10

<210> SEQ ID NO 80
<211> LENGTH: 20
<212> TYPE: PRT
<213> ORGANISM: Artificial Sequence
<220> FEATURE:
<223> OTHER INFORMATION: Synthetic reporter molecule sequence

<400> SEQUENCE: 80

His His His His His His Arg Cys Gly Pro Ala Gly Leu Arg Gly Leu
1               5                   10                  15

Glu Glu Glu Glu
            20

<210> SEQ ID NO 81
<211> LENGTH: 12
<212> TYPE: PRT
<213> ORGANISM: Artificial Sequence
<220> FEATURE:
<223> OTHER INFORMATION: Synthetic reporter molecule sequence

<400> SEQUENCE: 81

His His His His His His Arg Cys Gly Pro Ala Gly
1               5                   10
```

<210> SEQ ID NO 82
<211> LENGTH: 16
<212> TYPE: PRT
<213> ORGANISM: Artificial Sequence
<220> FEATURE:
<223> OTHER INFORMATION: Synthetic reporter molecule sequence

<400> SEQUENCE: 82

Gly Ala Gly Cys Arg Val Pro Leu Ser Leu Thr Met Gly Asp Asp Gly
1               5                   10                  15

<210> SEQ ID NO 83
<211> LENGTH: 21
<212> TYPE: PRT
<213> ORGANISM: Artificial Sequence
<220> FEATURE:
<223> OTHER INFORMATION: Synthetic reporter molecule sequence

<400> SEQUENCE: 83

His His His His His His His Arg His Arg Cys Val Pro Leu Ser Leu
1               5                   10                  15

Thr Met Gly Glu Glu
            20

<210> SEQ ID NO 84
<211> LENGTH: 14
<212> TYPE: PRT
<213> ORGANISM: Artificial Sequence
<220> FEATURE:
<223> OTHER INFORMATION: Synthetic reporter molecule sequence

<400> SEQUENCE: 84

His His His His His His Arg His Arg Cys Val Pro Leu Ser
1               5                   10

<210> SEQ ID NO 85
<211> LENGTH: 17
<212> TYPE: PRT
<213> ORGANISM: Artificial Sequence
<220> FEATURE:
<223> OTHER INFORMATION: Synthetic reporter molecule sequence

<400> SEQUENCE: 85

Gly Ala Gly Cys His His His Val Pro Leu Ser Leu Tyr Ser Gly Asp
1               5                   10                  15

Gly

<210> SEQ ID NO 86
<211> LENGTH: 21
<212> TYPE: PRT
<213> ORGANISM: Artificial Sequence
<220> FEATURE:
<223> OTHER INFORMATION: Synthetic reporter molecule sequence

<400> SEQUENCE: 86

His His His His His His Glu Glu Glu Cys Val Pro Leu Ser Leu Tyr
1               5                   10                  15

Ser Gly Lys Lys Lys
            20

<210> SEQ ID NO 87
<211> LENGTH: 14
<212> TYPE: PRT
<213> ORGANISM: Artificial Sequence

```
<220> FEATURE:
<223> OTHER INFORMATION: Synthetic reporter molecule sequence

<400> SEQUENCE: 87

His His His His His His Glu Glu Glu Cys Val Pro Leu Ser
1               5                   10

<210> SEQ ID NO 88
<211> LENGTH: 17
<212> TYPE: PRT
<213> ORGANISM: Artificial Sequence
<220> FEATURE:
<223> OTHER INFORMATION: Synthetic reporter molecule sequence

<400> SEQUENCE: 88

His His His His His His Cys Lys Cys Gly Ala Ala Asn Leu Val Arg
1               5                   10                  15

Gly

<210> SEQ ID NO 89
<211> LENGTH: 13
<212> TYPE: PRT
<213> ORGANISM: Artificial Sequence
<220> FEATURE:
<223> OTHER INFORMATION: Synthetic reporter molecule sequence

<400> SEQUENCE: 89

His His His His His His Cys Lys Cys Gly Ala Ala Asn
1               5                   10

<210> SEQ ID NO 90
<211> LENGTH: 26
<212> TYPE: PRT
<213> ORGANISM: Artificial Sequence
<220> FEATURE:
<223> OTHER INFORMATION: Synthetic reporter molecule sequence

<400> SEQUENCE: 90

His His His His His His Glu Glu Glu Glu Glu Cys Gly Pro Gln Gly
1               5                   10                  15

Leu Ala Gly Gln Arg Gly Ile Val Glu Glu
            20                  25

<210> SEQ ID NO 91
<211> LENGTH: 18
<212> TYPE: PRT
<213> ORGANISM: Artificial Sequence
<220> FEATURE:
<223> OTHER INFORMATION: Synthetic reporter molecule sequence

<400> SEQUENCE: 91

His His His His His His Glu Glu Glu Glu Glu Cys Gly Pro Gln Gly
1               5                   10                  15

Leu Ala

<210> SEQ ID NO 92
<211> LENGTH: 18
<212> TYPE: PRT
<213> ORGANISM: Artificial Sequence
<220> FEATURE:
<223> OTHER INFORMATION: Synthetic reporter molecule sequence

<400> SEQUENCE: 92

His His His His His His Cys Asp Glu Cys Gly Pro Ala Gly Leu Arg
1               5                   10                  15
```

Leu Ala

<210> SEQ ID NO 93
<211> LENGTH: 14
<212> TYPE: PRT
<213> ORGANISM: Artificial Sequence
<220> FEATURE:
<223> OTHER INFORMATION: Synthetic reporter molecule sequence

<400> SEQUENCE: 93

His His His His His His Cys Asp Glu Cys Gly Pro Ala Gly
1               5                   10

<210> SEQ ID NO 94
<211> LENGTH: 17
<212> TYPE: PRT
<213> ORGANISM: Artificial Sequence
<220> FEATURE:
<223> OTHER INFORMATION: Synthetic reporter molecule sequence

<400> SEQUENCE: 94

Gly Ala Gly Cys Arg His Gly Leu Ala Gly Leu Ala Gly Ala His His
1               5                   10                  15

Cys

<210> SEQ ID NO 95
<211> LENGTH: 24
<212> TYPE: PRT
<213> ORGANISM: Artificial Sequence
<220> FEATURE:
<223> OTHER INFORMATION: Synthetic reporter molecule sequence

<400> SEQUENCE: 95

His His His His His His Cys Glu Asp Cys Ser Leu Leu Arg Ser Arg
1               5                   10                  15

Met Val Pro Asn Phe Asn Cys Cys
            20

<210> SEQ ID NO 96
<211> LENGTH: 14
<212> TYPE: PRT
<213> ORGANISM: Artificial Sequence
<220> FEATURE:
<223> OTHER INFORMATION: Synthetic reporter molecule sequence

<400> SEQUENCE: 96

His His His His His His Arg Cys Ser Leu Leu Arg Ser Arg
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Synthetic reporter molecule sequence

<400> SEQUENCE: 97

Gly Ala Gly Cys Leu Glu Val Leu Phe Val Leu Gly Gly
1               5                   10

<210> SEQ ID NO 98
<211> LENGTH: 23
<212> TYPE: PRT
<213> ORGANISM: Artificial Sequence
<220> FEATURE:

<223> OTHER INFORMATION: Synthetic reporter molecule sequence

<400> SEQUENCE: 98

His His His His His His Lys Glu Lys Cys Ser Leu Leu Ile Phe Arg
1               5                   10                  15

Ser Trp Ala Asn Phe Asn Lys
            20

<210> SEQ ID NO 99
<211> LENGTH: 16
<212> TYPE: PRT
<213> ORGANISM: Artificial Sequence
<220> FEATURE:
<223> OTHER INFORMATION: Synthetic reporter molecule sequence

<400> SEQUENCE: 99

His His His His His His Lys Glu Lys Cys Ser Leu Leu Ile Phe Arg
1               5                   10                  15

<210> SEQ ID NO 100
<211> LENGTH: 19
<212> TYPE: PRT
<213> ORGANISM: Artificial Sequence
<220> FEATURE:
<223> OTHER INFORMATION: Synthetic reporter molecule sequence

<400> SEQUENCE: 100

Gly Ala Gly Cys His Lys His Lys Glu Val Val Leu Val Ala Leu Ala
1               5                   10                  15

Arg His Gly

<210> SEQ ID NO 101
<211> LENGTH: 19
<212> TYPE: PRT
<213> ORGANISM: Artificial Sequence
<220> FEATURE:
<223> OTHER INFORMATION: Synthetic reporter molecule sequence

<400> SEQUENCE: 101

Gly Ala Gly Cys His Lys Arg Lys Arg Gly Leu Glu Gly Ala Asp Asp
1               5                   10                  15

Arg His Gly

<210> SEQ ID NO 102
<211> LENGTH: 21
<212> TYPE: PRT
<213> ORGANISM: Artificial Sequence
<220> FEATURE:
<223> OTHER INFORMATION: Synthetic reporter molecule sequence

<400> SEQUENCE: 102

His His His His His His Asp Asp Asp Asp Asp Asp Cys Gly Pro
1               5                   10                  15

Arg Ala Gly Arg Arg
            20

<210> SEQ ID NO 103
<211> LENGTH: 17
<212> TYPE: PRT
<213> ORGANISM: Artificial Sequence
<220> FEATURE:
<223> OTHER INFORMATION: Synthetic reporter molecule sequence

<400> SEQUENCE: 103

```
His His His His His His Asp Asp Asp Asp Asp Asp Asp Cys Gly Pro
1               5                   10                  15

Arg

<210> SEQ ID NO 104
<211> LENGTH: 18
<212> TYPE: PRT
<213> ORGANISM: Artificial Sequence
<220> FEATURE:
<223> OTHER INFORMATION: Synthetic reporter molecule sequence

<400> SEQUENCE: 104

Gly Ala Gly Cys Arg Arg Arg Arg Glu Leu Leu Gly Ser Pro Pro Asp
1               5                   10                  15

Asp Gly

<210> SEQ ID NO 105
<211> LENGTH: 27
<212> TYPE: PRT
<213> ORGANISM: Artificial Sequence
<220> FEATURE:
<223> OTHER INFORMATION: Synthetic reporter molecule sequence

<400> SEQUENCE: 105

His His His His His His Glu Glu Glu Glu Glu Glu Glu Cys Ser Gly
1               5                   10                  15

Val Val Ile Ala Thr Val Ile Val Ile Thr Lys
            20                  25

<210> SEQ ID NO 106
<211> LENGTH: 20
<212> TYPE: PRT
<213> ORGANISM: Artificial Sequence
<220> FEATURE:
<223> OTHER INFORMATION: Synthetic reporter molecule sequence

<400> SEQUENCE: 106

His His His His His His Glu Glu Glu Glu Glu Glu Glu Cys Ser Gly
1               5                   10                  15

Val Val Ile Ala
            20

<210> SEQ ID NO 107
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 107

Gly Cys Tyr Tyr Lys Lys
1               5

<210> SEQ ID NO 108
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 108

Gly Cys Glu His His
1               5
```

MICROFLUIDICS-BASED NANOBIOSENSORS AND DEVICES

CROSS-REFERENCE TO RELATED APPLICATIONS

The present application is the U.S. National Stage of International Patent Application No. PCT/US2017/062304, filed Nov. 17, 2017, which claims the priority benefit of U.S. Provisional Patent Application Ser. No. 62/424,224, filed Nov. 18, 2016, entitled MICROFLUIDICS-BASED NANOBIOSENSORS, and Ser. No. 62/455,853, filed Feb. 7, 2017, entitled MICROFLUIDIC ISOELECTRIC FOCUSING DEVICE, each of which is incorporated by reference in its entirety herein.

SEQUENCE LISTING

The following application contains a sequence listing in computer readable format (CRF), submitted as a text file in ASCII format entitled "Sequence Listing," created on Nov. 17, 2017, as 28 KB. The content of the CRF is hereby incorporated by reference.

BACKGROUND OF THE INVENTION

Field of the Invention

The present invention relates to nanobiosensors and microfluidics techniques for detecting one or more target analyte(s) in a biological sample.

Description of Related Art

Molecular-based screening techniques and liquid-based biopsy approaches that can be used to detect and quantify various biomarkers are promising techniques for non-invasive detection and staging of cancer and various other diseases. For example, extracellular proteases are associated with a variety of disease processes. In particular, increased activity of matrix metalloproteinases and cathepsins have been reported for a variety of diseases and that makes them potential biomarker candidates. Similarly, the protein kinase superfamily is dysregulated in cancer and other malignancies. Furthermore, many specific kinases have functional roles in solid tumors and numerous other inflammatory diseases. When these diseases are treated, kinome remodeling modulates sensitivity to drugs, leading to drug resistance in numerous cancers.

While significant progress has been made for the diagnoses of various conditions, including cancers, these techniques are inadequate to detect cancers at early stage of development mainly due to their failure to detect molecular markers at the low concentrations associated with the disease onset. Although molecular-based diagnostics can, principally, help distinguish early stage lung cancer from benign nodules that are incidentally detected by a CT scan, the impact has been incremental reducing the number of false positives by 32%. Currently, there are no devices/sensing platforms that can be used in clinical diagnosis and/or point-of-care-detection to monitor the onset or recurrence of cancer utilizing biomarkers present in biofluid samples collected by minimally invasive or non-invasive sampling techniques (e.g. peripheral blood, saliva, mucus etc.) with limits of detection (LODs) sufficient to detect solid tumor cancers at the 0 and 1 stages.

SUMMARY OF THE INVENTION

The present invention is broadly concerned with methods of microfluidic detection of a target analyte in a biological sample collected from a subject.

The methods generally comprise providing a microfluidic device comprising a planar substrate comprising a sample inlet well positioned above a sample chamber in or on the substrate and a detection chamber in fluid communication with the sample chamber via a microfluidic channel extending from the sample chamber to the detection chamber. A washing or wash chamber positioned along the microfluidic channel intermediate to the sample chamber and the detection chamber. The device also includes a magnet positioned external and adjacent to the microfluidic channel (e.g., generally underneath the channel), wherein the magnet is translatable along a plane parallel and to the plane of the microfluidic channel. In other words, the magnet is configured and positioned such that it can be slid back and forth underneath the microfluidic channel and essentially follow the same linear/horizontal path as the channel. The magnet could also be laterally movable to follow the path of one or more inlet channels or outlet channels extending from the main microfluidic channel. The biological sample collected from the subject is incubated with a first nanobiosensor in the sample chamber for a time period and under conditions (e.g., ambient conditions or slightly elevated temperatures) sufficient for the target analyte (if present) in the biological sample to interact with the first nanobiosensor. The first nanobiosensor comprises a magnetic nanoparticle releasably attached to a plurality of reporter molecules (which each contain peptide sequences specific for the target analyte). Thus, the magnet can be rotated or manipulated to magnetically manipulate and move the nanobiosensor. It will be appreciated that the magnet can be used to facilitate mixing of the nanobiosensor and biological sample during incubation.

The incubated sample and first nanobiosensor is then transferred to the wash chamber. This can be accomplished with a valve system or by using the magnet's attractive forces to "pull" the sample to the wash chamber. A wash fluid is introduced into the wash chamber to yield a first washed nanobiosensor. In general, this involves removing at least a portion of the biological sample matrix and unreacted components from the system, such as through an outlet channel to a wash outlet chamber, so that only the washed nanobiosensors are left in the wash chamber (along with residual sample, cleaved reporter molecules, buffer, wash fluid, etc.). This step is facilitated by maintaining the magnet in a fixed position adjacent the wash chamber (e.g., underneath) to magnetically "hold" the nanobiosensors in a fixed position while the wash fluid moves through the wash chamber and exits the outlet channel into the waste chamber. It will also be appreciated that this step changes the relative concentration of the nanobiosensor in the biological sample, as a portion of the biological sample is removed, leaving a higher concentration of nanobiosensor behind for the subsequent detection step.

Next, the first washed nanobiosensor is magnetically transferred to the detection chamber. This step is facilitated by translating the magnet along a plane parallel to the microfluidic channel from a position adjacent the wash chamber to a position adjacent the detection chamber. In other words, this can involve sliding the magnet along a linear path underneath the microfluidic channel along the linear path followed by the channel, while the magnetic is in sufficient proximity to the channel so that the attractive forces of the magnetic will magnetically guide (or pull) the nanobiosensors from the wash chamber to the detection chamber.

In the detection chamber, the nanobiosensor is essentially cleaved apart so that the magnetic nanoparticle can be removed from the detection chamber. This generally involves separating or uncoupling the nanoparticle from its respective reporter molecules to yield a plurality of individual separated reporter molecules and a delinked or uncoupled nanoparticle.

The delinked (or uncoupled) nanoparticle is then magnetically removed from the detection chamber by translating the magnet along a plane parallel to the microfluidic channel away from the detection chamber. In other words, this can involve sliding the magnet backwards along the linear path underneath the microfluidic channel along the linear path followed by the channel, while the magnetic is in sufficient proximity to the channel so that the attractive forces of the magnetic will magnetically guide (or pull) the nanobiosensors from the detection chamber back into the detection chamber. It is envisioned that the magnet could also be translated laterally to move the nanoparticles out of the detection chamber via a lateral outlet channel extending from the detection chamber and/or the magnet could continue along the initial path of travel so that the nanoparticles would exit the distal end of the detection chamber (opposite from the wash chamber), instead of returning to the wash chamber.

Once the nanoparticles have been removed from the detection chamber, the presence or absence of reacted and/or unreacted separated reporter molecules that remain in the chamber is then detected, wherein the presence and/or absence of a given reacted and/or unreacted reporter molecule is indicative of interaction (or presence/absence) of the target analyte with the reporter molecules.

It will be appreciated that the methods of the invention are particularly suited for detecting a plurality of target analytes in a single sample. This is achieved through the use of a plurality of different types of nanobiosensors with different reporter molecules specific to a different target analytes. Further, detection techniques can generate a linearly spaced array of different reporter molecules at respective locations in the detection chamber, which can be "read" similar to a bar code reader.

Embodiments of the invention are also concerned with microfluidic devices for detection of a target analyte in a biological sample. The microfluidic devices generally comprise a planar substrate comprising a sample inlet well positioned above a sample chamber in or on the substrate and a detection chamber in fluid communication with the sample chamber via a microfluidic channel extending from the sample chamber to the detection chamber; and a washing chamber positioned along the microfluidic channel intermediate to the sample chamber and the detection chamber; and a magnet positioned external and adjacent to the microfluidic channel, wherein the magnet is translatable along a plane parallel and to the plane of the microfluidic channel. For IEF detection, the device further comprises in fluid communication with the detection chamber: an ampholyte inlet configured to introduce a high-resolution ampholyte mixture into the detection chamber, a catholyte inlet configured to introduce a catholyte mixture into the detection chamber, an anolyte inlet configured to introduce a high-resolution anolyte mixture into the detection chamber, and a pressure fill inlet valve. The detection chamber can further comprise one or more inlets for applying an electrical current to the detection chamber.

Embodiments described herein are also concerned with nanobiosensors for detection of a target analyte in a biological sample. The nanobiosensors comprise a magnetic nanoparticle releasably attached to a reporter molecule via a release unit, wherein the reporter molecule is an oligopeptide comprising a target analyte recognition sequence, detectable label, and one or more optional pI tag(s).

DETAILED DESCRIPTION

Figure 1A:
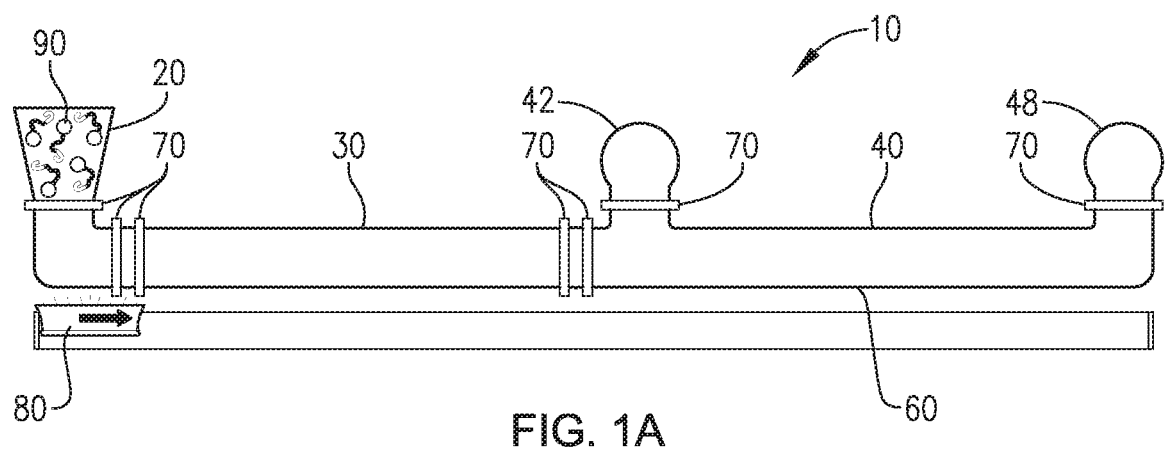
FIG. 1A is a schematic side view of a microfluidic device in use accordance with one embodiment of the present invention.

The present invention is concerned with nanobiosensors and microfluidics techniques for detecting one or more target analyte(s) in a biological sample. The invention leverages the use of nanobiosensors comprising magnetic nanoparticles bound to a reporter molecule via a release unit. In one or more embodiments, each nanobiosensor comprises a plurality of reporter molecules attached to a single central nanoparticle via respective release units. In particularly preferred embodiments, a plurality of a single type of reporter molecule may be attached to each nanoparticle. In other embodiments, however, a plurality of different types of reporter molecules may also be attached to each nanoparticle. Regardless a plurality of different types of reporter molecules are preferably used so that the assays can analyze a plurality of different types of target analytes in a single biological sample.

In general, a biological sample is collected from a subject and prepared for analysis. The nanobiosensors are contacted with a biological sample for a period of time sufficient for the target analyte (if present in the sample) to interact with the reporter molecules in the nanobiosensors. The nanobiosensors can advantageously be directly added to raw samples (biospecimens). The reacted sample is then washed with a wash solution, and the washed nanobiosensors are then transferred to a detection chamber. In the detection chamber, the reporter molecule is released from the nanobiosensor, and the nanoparticles are transferred out of the detection chamber (e.g., back to the wash chamber), while the reacted and unreacted reporter molecules remain in the detection chamber. Any reacted reporter molecules can then be detected in the detection chamber, and the presence and/or absence of reacted/unreacted reporter molecules at designated locations in the detection chamber (and their relative intensities) can be correlated with a prognosis or diagnosis if desired.

The nanoparticle facilitates transport of the nanobiosensor out of the sample matrix after reaction, which reduces matrix effects and thus noise in the final optical readout. In addition, the signal is further enhanced as the concentration of the nanobiosensors are increased ~$10^6$ (1,000,000) fold from the starting sample volume (e.g., ~1 to about 5 mL) into a smaller concentrated volume (e.g., ~nL) focused band as explained below. The nanoparticles can be manipulated (mixed and transported) by moving or rotating an external magnet, thus varying the external magnetic field, which can also be used to mix the nanobiosensor with the sample. While the nanoparticles can assist with mixing and transporting the peptide substrate they will hinder separation due to their charge and size dispersion and thus need to be separated from the reporter molecule before separation and detection. The release unit allows the reporter molecules, both uncleaved/cleaved or unmodified/modified to be delinked from the nanoparticle before the detection technique is applied to the assay.

Magnetic Nanoparticle

The term "nanoparticle" as used herein refers to nanocrystalline particles that can optionally be surrounded by a metal and/or nonmetal nanolayer shell. The nanoparticles are preferably metal nanoparticles: metal, metal alloy, metal oxide, or core/shell metal nanoparticles (e.g. $Fe_2O_3$, $Fe_3O_4$), and specifically ferromagnetic metal nanoparticles. Thus, the metal nanoparticles comprise any type of ferromagnetic metal (including elemental metal) or metal alloy: iron (Fe), nickel (Ni), cobalt (Co), certain alloys of rare-earth metals, and the oxides (e.g., FeO, $Fe_3O_4$, $Fe_2O_3$, $Fe_xO_y$ (non-stoichiometric iron oxide), NiO), hydroxides, sulfides, selenides, and tellurides of the foregoing, and combinations thereof.

Suitable nanoparticles preferably have a diameter of from about 1 nm to about 100 nm, more preferably from about 10 nm to about 50 nm, and even more preferably from about 20 nm to about 40 nm. The nanoparticles may also include an additional metal, so long as the magnetic property of the nanoparticle is not impaired, including methods selected from the group consisting of gold (Au), silver (Ag), copper (Cu), palladium (Pd), platinum (Pt), rhodium (Rh), iridium (Ir), iron (Fe), ruthenium (Ru), osmium (Os), manganese (Mn), rhenium (Re), scandium (Sc), titanium (Ti), vanadium (V), chromium (Cr), zinc (Zn), yttrium (Y), zirconium (Zr), niobium (Nb), molybdenum (Mo), technetium (Tc), cadmium (Cd), lanthanum (La), lutetium (Lu), hafnium (Hf), tantalum (Ta), tungsten (W), actinium (Ac), lawrencium (Lr), rutherfordium (Rf), dubnium (Db), seaborgium (Sg), bohrium (Bh), Hassium (Hs), meitnerium (Mt), darmstadtium (Ds), roentgenium (Rg), ununbium (Uub), selenium (Se), and the oxides (e.g., CuO, $Ag_2O$, $Mn_2O_3$), hydroxides, sulfides, selenides, and tellurides of the foregoing, and combinations thereof.

In some embodiments, metal nanoparticles will be bi- or para-magnetic and comprise a metal or metal alloy core and a metal shell. Core/shell metal nanoparticles preferably comprise a metal or metal alloy core and a metal shell. Preferred cores are selected from the group consisting of Au, Ag, Cu, Co, Fe, and Pt. Even more preferably, the metal nanoparticles feature a strongly paramagnetic Fe core. Preferred shells are selected from the group consisting of Au, Ag, Cu, Co, Fe, Pt, the metal oxides (e.g., FeO, $Fe_3O_4$, $Fe_2O_3$, $Fe_xO_y$ (non-stoichiometric iron oxide), CuO, $Cu_2O$, NiO, $Ag_2O$, $Mn_2O_3$) thereof, and combinations thereof. Particularly preferred metal core/shell combinations are selected from the group consisting of Fe/Au, Fe(0)/$Fe_3O_4$, and Au/$Fe_2O_3$. A particularly preferred metal nanoparticle is a superparamagnetic Fe/$Fe_3O_4$ core shell nanoparticle. More preferably, the nanoparticles feature an iron(0) core, which is more magnetic than iron oxide, based upon coercivity. This means that smaller nanoparticles can be used (diameter less than about 10 nm), which have the same or greater magneticity than larger iron oxide nanoparticles (diameter of about 200 nm).

In one or more embodiments, the core of the metal nanoparticle preferably has a diameter of from about 5 nm to about 100 nm, more preferably from about 20 nm to about 50 nm and more preferably from about 30 nm to about 40 nm. The metal shell of the core/shell nanoparticle preferably has a thickness of from about 1 nm to about 10 nm, and more preferably from about 2 nm to about 5 nm. The nanoparticles preferably have a Brunauer-Emmett-Teller (BET) multipoint surface area of from about 20 $m^2/g$ to about 500 $m^2/g$, more preferably from about 50 $m^2/g$ to about 350 $m^2/g$, and even more preferably from about 60 $m^2/g$ to about 80 $m^2/g$. The nanoparticles preferably have a Barret-Joyner-Halenda (BJH) adsorption cumulative surface area of pores having a width between 17.000 Å and 3000.000 Å of from about 20 $m^2/g$ to about 500 $m^2/g$, and more preferably from about 50 $m^2/g$ to about 150 $m^2/g$. The nanoparticles also preferably have a BJH desorption cumulative surface area of pores having a width between 17.000 Å and 3000.000 Å of from about 50 $m^2/g$ to about 500 $m^2/g$, and more preferably from about 50 $m^2/g$ to about 150 $m^2/g$. The nanoparticle population is preferably substantially monodisperse, with a very narrow size/mass size distribution. More preferably, the nanoparticle population has a polydispersity index of from about 1.2 to about 1.05. It is particularly preferred that the nanoparticles used in the inventive nanoplatforms are discrete particles. That is, clustering of nanocrystals (i.e., nanocrystalline particles) is preferably avoided.

The nanoparticles can be stabilized or non-stabilized. Stabilized nanoparticles preferably comprise an organic monolayer surrounding the nanoparticle core. The term "stabilized" as used herein means the use of a ligand shell or monolayer to coat, protect (e.g., from bio-corrosion), or impart properties (e.g., water solubility) to, the nanoparticle. The monolayer can be comprised of several of the same ligands (i.e., homoligand) or of mixed ligands. Various techniques for attaching ligands to the surface of various nanoparticles are known in the art. For example, nanoparticles may be mixed in a solution containing the ligands to promote the coating of the nanoparticle. Alternatively, coatings may be applied to nanoparticles by exposing the nanoparticles to a vapor phase of the coating material such that the coating attaches to or bonds with the nanoparticle. Preferably, the ligands attach to the nanoparticle through covalent bonding. The number of ligands required to form a monolayer will be dependent upon the size of the nanoparticle.

The ligands comprise functional groups that are attracted to the nanoparticle's metal surface. Preferably, the ligands comprise at least one group selected from the group consisting of thiols, alcohols, nitro compounds, phosphines, phosphine oxides, resorcinarenes, selenides, phosphinic acids, phosphonicacids, sulfonic acids, sulfonates, carboxylic acids, disulfides, peroxides, amines, nitriles, isonitriles, thionitiles, oxynitriles, oxysilanes, alkanes, alkenes, alkynes, aromatic compounds, and seleno moieties. Preferred organic monolayers are selected from the group consisting of alkanethiolate monolayers, aminoalkylthiolate monolayers, alkylthiol sulfate monolayers, and organic phenols (e.g., dopamine, 3,4-dihydroxyphenylacetic acid, 3,4-dihydroxyphenylpropionic acids and homologues/derivatives thereof). The thickness of the organic monolayer is preferably less than about 10 nm, and more preferably less than about 5 nm. Particularly preferred stabilized nanoparticles are selected from the group consisting of trioctylphosphinoxide-stablized nanoparticles, amine-stabilized nanoparticles, carboxylic-acid-stabilized nanoparticles, phosphine-stabilized nanoparticles, thiol-stabilized nanoparticles, aminoalkylthiol-stabilized nanoparticles, and organic phenol-stabilized nanoparticles.

For attachment to the release unit, the preferred ligands will preferably readily react with the thiol group of a terminal cysteine. The nanoparticle surface will preferably be essentially completely covered with ligands. That is, at least about 70%, preferably at least about 90%, and more preferably about 100% of the surface of the nanoparticle will have attached ligands. The number of ligands required to form a monolayer will be dependent upon the size of the nanoparticle (and monolayer), and can be calculated using molecular modeling or ligand modeling methods.

Various techniques for attaching ligands to the surface of various nanoparticles are known in the art. For example, nanoparticles may be mixed in a solution containing the ligands to promote the coating of the nanoparticle surface. Alternatively, coatings may be applied to nanoparticles by exposing the nanoparticles to a vapor phase of the coating material such that the coating attaches to or bonds with the nanoparticle. Preferably, the ligands attach to the nanoparticle through covalent bonding. Preferred nanoparticles are characterized as 3,4-dihydroxyphenylacetic acid-covered, water-dispersible iron/iron oxide core/shell nanoparticles.

Release Unit

The nanoparticle is attached to the reporter molecule via a release unit, which can be any suitable linkage between the reporter molecule and nanoparticle, so that the nanoparticle can be separated from the reporter molecule after exposure to the biological sample (and washing) and can be removed from the detection chamber. It will be appreciated that a variety of approaches can be used to releasably attach the reporter molecule to the magnetic nanoparticle, provided that the release mechanism is not detrimental to the functionality of the reporter molecule (e.g., specificity of the reporter molecule for the target analyte). Further, the release unit itself should not interact with or be modified by the biological sample itself (or any of its analytes, e.g., as an enzyme substrate). That is, as will be appreciated below, even after incubation with the biological sample and/or washing, the release unit (and thus, the linkage between the reporter molecule and nanoparticle) remains intact, such that the reporter molecule is not released until after the nanobiosensor is transferred to the detection chamber.

A number of exemplary approaches for various release units are described and demonstrated herein.

In one or more embodiments, the reporter molecule is attached to the nanoparticle via a reducible disulfide bridge. In one or more embodiments, the reporter molecule and nanoparticle can be joined to the nanoparticle by a disulfide bridge via respective cysteines residues. Disulfide bonds can be reductively cleaved upon addition of, for example, reducing agents, such as dithiothreitol (DTT), water-soluble phosphorous (III) reagents (e.g. THPP (tris-hydroxypropyl-phosphine), mercaptoethanol, mercaptoethylamine, or tris(2-carboxyethyl)phosphine (TCEP), and the like.

In one or more embodiments, the reporter molecule is attached to the nanoparticle via a pH-sensitive linkage. For example, certain bonds become unstable at certain pH ranges, such as esters (pH>9-10), hydrazones (pH>6-8), or acetals (pH<5), etc. In contrast, the reporter molecule includes oligopeptides featuring stable amide bonds in their backbones, which are essentially stable in the pH-range from 1 to 12.4. Thus, the reporter molecule will not be affected by changes in pH in the detection chamber.

In one or more embodiments, the reporter molecule is attached to the nanoparticle via a photosensitive linkage. Photorelease of the reporter molecule is an alternative to chemical transformations, which occur in the dark. Thus, in one or more embodiments, the release unit is a "photorelease unit" that absorbs one (or several) photon(s) upon exposure to activating radiation (e.g., light source), which triggers a chemically defined release reaction, resulting in cleavage of the linkage between the nanoparticle and reporter molecule. Although, principally, mono- or higher photonic processes can be used for photorelease purposes, monophotonic processes are preferred, because they possess distinctly higher release quantum yields (0.01 to unity). Exemplary photorelease units can be attached to the nanoparticle via a —NH—, —CONH—, —O—, —S—, or —$C_nH2_n$— bond. Boron-Dipyrromethene (BODIPY)-mediated photorelease is one example, where BODIPY serves as an organic bridging unit between the magnetic nanoparticle and reporter molecule that releases the C-terminal end of the reporter molecule oligopeptide upon monophotonic excitation with red laser light. Another example is 8-cyano-7-hydroxyquinolinyl (CyHQ)-mediated release, which contains a photoremovable protecting group that releases N- or C-terminal histidine groups upon monophotonic excitation with blue light or bi-photonic NIR excitation. Another example is ruthenium-polypyridyl-mediated photorelease, which reacts under mono- or diphotonic excitation. Accessible ligand-centered states lead to photodissociation reaction of pyridine-type ligands upon exposure to blue or NIR laser diodes.

In one or more embodiments, the reporter molecule is attached to the nanoparticle via a thermosensitive linkage. Thermal release of the reporter molecule occurs after photons are absorbed by a plasmonic nanoparticle, or after thermal heating, A/C, or radiofrequency hyperthermia has been applied. The heat that is generated in the nanoparticle through light absorption will be able to facilitate thermal release reactions, such as the cleavage of thermally unable bonds or adducts (e.g. imines or Diels-Alder products etc.) or strand separation ("melting") of DNA double-strands or supramolecular LEGO peptide sequences and phenylalanine-isoleucin "zippers" that may form a portion of the release unit. Exemplary thermal release units can be attached to the nanoparticle via a —NH—, —CONH—, —O—, —S—, —($CH_2CH_2$—O)—, or —$C_nH2_n$— bond.

Reporter Molecule

The reporter molecule is a peptide probe or sensing peptide sequence comprising a recognition sequence, detectable label, and optional pI tag(s). The recognition sequence is typically an oligopeptide sequence that has specificity for and is recognized by the target analyte, such as, for example, an enzyme substrate sequence. As used here, the phrase "specificity for" is intended to differentiate the recognition sequences from non-specific binding or reactions between molecules, and means that the set of specific target analytes for which the recognition sequence can interact is limited, and in some cases even exclusive, such that neither binding nor enzymatic cleavage occurs at an appreciable rate with any other molecule except for the target analyte. Short oligopeptide sequences are preferably used for the recognition sequences including sequence segments with high specificity for the target analyte. Exemplary oligopeptides are preferably less than 50 amino acid residues in length, and more preferably from about 5 to about 20 amino acid residues.

In one or more embodiments, the recognition sequence comprises, consists essentially, or even consists of a "protease consensus sequence," which refers to an enzyme substrate (peptide sequence) that undergoes enzymatic cleavage in the presence of the target analyte (i.e., protease, esterase, etc.). Such consensus sequences are described, for example, in U.S. Pat. Nos. 8,969,027 and 9,216,154, U.S. Publication No. 2017/0219548, each incorporated by reference herein to the extent not inconsistent with the present disclosure. In one or more embodiments, the recognition sequence comprises, consists essentially, or even consists of a recognition sequence for detection of enzymatic posttranslational modification described in WO 2016/149637, incorporated by reference herein to the extent not inconsistent with the present disclosure. In the presence of the target enzyme, the enzyme modifies the recognition sequence (without cleavage), and more particularly modifies both the primary structure (amino acid residues and metabolic products) and the secondary structure of the recognition sequence. Such "modification" or "posttranslational modification" as used herein, refers to conversion or transformation of the amino acid residues (and particularly the side chains) in the substrate sequence to a different form and/or different residue. This, in turn, extends, "unfolds," or "unravels" the secondary structure and/or increases and/or decreases the mobility of the recognition sequence. In one or more embodiments, the recognition sequence comprises, consists essentially, or even consists of a supramolecular recognition sequence to detect physical binding without chemical modification or enzymatic cleavage. In particular, the target protein binds to the supramolecular recognition sequence linearly, such that the initial folded secondary structure, such as an alpha-helix and/or beta-sheet structure, is modified and linearly extends or unfolds. In each instance, interaction of the target analyte (e.g., protein, enzyme, etc.) with the recognition sequence gives rise to a detectable change in the nanobiosensor, which is indicative of the presence of the target analyte.

Exemplary recognition sequences are listed in Table 1 below along with their corresponding target analyte.

TABLE 1

Recognition sequence examples

| | Recognition Sequence(s) | SEQ ID NO: | Accession No. |
|---|---|---|---|
| Cytokine/Chemokine Targets | | | |
| CCL 2 | CQEQFWW | 1 | P13500 |
| MCP-1[a] | PYFPRGSSYQGWN | 2 | P13500 |
| CCL 3 | CCIQNQ | 3 | P10147 |
| CCL 4 | AWYQPQFE | 4 | P13236 |
| CCL 21 | EQQKRN | 5 | O00585 |
| CXCL 2 | CNHGKFYC | 6 | P19875 |
| CXCL 5 | NIYCNIAY | 7 | P42830 |
| CXCL 8 (IL-8) | KAYRWEFI | 8 | P10145 |
| CXCL 9 | IQNSGAPCH | 9 | Q07325 |
| HSP 27 | WQEAKNANQM | 10 | Q5S1U1 |
| HSP 70 | RHQKTYSF | 11 | P0DMV8 |
| HSP 90 | XLPPHWAGAL | 12 | P02829 |
| MIF | XLPPHWAFAL | 13 | P14174 |
| Calprotectin | LTELEKALNSIIDVYHKYSLIKGNFHAV | 14 | S100A9 |
| CCL20[b] | GESMNFSDVFDSSEDYFVSVNTSYYSVDSE GTQWVVCQQFG | 15 16 | P78556 |
| GCSF[c] | PGHWSDWSPS | 17 | P09919 |
| IL-6 | YFPEPVTVSGAGTFPAVLGSGQPPGKGL TAVYYCANRAGWGMGDYWGQGTQVT TASNYGAGYSTNDRHS NRPAQAWMLG | 18 19 20 21 | P05231 |
| IL-13 | AVYYCQQNNEDPRTFGGGTK AGDGYYPYAMDNW GWLPFGFILISAG YQQKPGQPPKL SVNWIRQPPGKALEWLAMIWGDGKIVYNS WLPFGFILIS | 22 23 24 25 26 27 | P35225 |
| IL1RL1[d] | TYYCQQWSGYPYTF | 28 | P14778 |
| MIP-1[e] | SHFPYSQYQFWKN | 29 | Q9BPZ7 |
| OSTF1[f] | DMSDTNWWKGTSKGRTGLIPSNYVAEQAE SIDNPL | 30 | Q92882 |
| TIMP-1[g] | IAGKLQSAGSALWTDQL | 31 | P01033 |
| TSLP[h] | SSPKHVRFSWHQDAVTVTC AKCCPCQQWW | 32 33 | Q960D9 |
| Enzyme Consensus Sequence | | | |
| ADAM 17 | LAQAVVSS | 34 | P78536 |
| ADAM 33 | GSQHIRAE | 35 | Q9BZ11 |
| Cathepsin B | SLLKSRMVPNFN | 36 | P07858 |
| Cathepsin D | GDSGLGRA | 37 | P07339 |
| Cathepsin E | EVALVALK | 38 | P14091 |
| Cathepsin K | LGLEGANL | 39 | P43235 |

TABLE 1-continued

Recognition sequence examples

| Recognition Sequence(s) | | SEQ ID NO. | Accession No. |
|---|---|---|---|
| Cathepsin L | AALGSAPG | 40 | P07711 |
| Cathepsin S | SLLIFRSWANFN | 41 | P25774 |
| Granzyme B | VEPNSLEE | 42 | P10144 |
| NE | GEPLSLLP | 43 | P08246 |
| MMP 1 | IPVSLRSG | 44 | P03956 |
| MMP 2 | IPVSLRSG | 44 | P08253 |
| MMP 3 | RPFSMIMG | 45 | P08254 |
| MMP 7 | VPLSLTMG | 46 | P09237 |
| MMP 8 | GPSGLRGA | 47 | P22894 |
| MMP 9 | VPLSLYSG | 48 | P14780 |
| MMP 11 | GAANLVRG | 49 | P24347 |
| MMP 12 | GVPLSLTMG | 50 | P34960 |
| MMP 13 | PQGLAGQRGIV | 51 | P33435 |
| MMP 14 | GPAGLRLA | 52 | P50281 |
| ALK | RDIYAAPFFRK | 53 | Q9UM73 |
| AURKB | AMERRRTSAARRSY | 54 | Q96GD4 |
| CDK2 | KARAAVSPQKRKA | 55 | P24941 |
| PKD2 | RARKRRLSAPPLASGD | 56 | Q504Y2 |
| MAPK1 | AKAGPPLSPRPPHVH | 57 | P28482 |
| JAK2 | DLFIPDNYLKMKPAP | 58 | O60674 |
| PLK1 | AELDPEDSMDMDMAP | 59 | P53350 |
| PLK3 | EDEAEELSDEDEELK | 60 | Q9H4B4 |
| ERK1/MAPK3 | AAGPAPLSPVPPVVH | 61 | P27361 |
| JunK2/MAPK9 | DASRPPPLSPLPSPRA | 62 | P45984 |
| ARG I/II | GRRRRRRG | 63 | P05089 (ARG1) P78540 (ARG2) |
| uPA | SGRSA | 64 | |

<sup>a</sup>Monocyte Chemoattractant Protein-1;
<sup>b</sup>Chemokine (C-C motif) ligand 20 (CCL20) or liver activation regulated chemokine (LARC) or Macrophage Inflammatory Protein-3 (MIP3A);
<sup>c</sup>Granulocyte colony-stimulating factor;
<sup>d</sup>Interleukin-1-receptor-like type 1;
<sup>e</sup>Macrophage Inflammatory Protein;
<sup>f</sup>Osteoclast Stimulating Factor-1;
<sup>g</sup>Metalloproteinase Inhibitor 1;
<sup>h</sup>Thymic stromal lymphopoietin.

The recognition sequences can include one or more spacer residues on the N- and/or C-terminal ends. For example, between 1 and 10 amino acids (any amino acids, naturally and non-naturally, L- and D-, or combinations thereof) can be used at one or both ends as spacers. Examples include N-terminal sequences such as GAG- and C-terminal sequences such as -AG.

The reporter molecule further includes a detectable label that generates a detectable signal which can be detected and correlated with presence (or absence) of the target analyte. Exemplary detectable labels include detectable particles that generate a detectable signal (e.g., optical or spectroscopic), such as fluorescence or color change, which can be perceived visually or measured with an appropriate instrument. Chromophore/luminophores suitable for use in the inventive assays include any organic or inorganic dyes, fluorophores, phosphophores, light absorbing nanoparticles (e.g., Au, Ag, Pt, Pd), combinations thereof, or the non-magnetic metalated complexes thereof. Preferably, the chromophore/luminophores have a particle size (maximum surface-to-surface dimension, i.e., diameter) of less than about 100 nm.

Suitable organic dyes are selected from the group consisting of coumarins, pyrene, cyanines, benzenes, N-methylcarbazole, erythrosin B, N-acetyl-L-tryptophanamide, 2,5-diphenyloxazole, rubrene, and N-(3-sulfopropyl)acridinium. Specific examples of preferred coumarins include 7-aminocoumarin, 7-dialkylamino coumarin, and coumarin 153. Examples of preferred benzenes include 1,4-bis(5-phenyloxazol-2-yl)benzene and 1,4-diphenylbenzene. Examples of preferred cyanines include oxacyanines, thiacyanines, indocyanins, merocyanines, and carbocyanines. Other exemplary cyanines include ECL Plus, ECF, C3-Oxacyanine, C3-Thiacyanine Dye (EtOH), C3-Thiacyanine Dye (PrOH), C5-Indocyanine, C5-Oxacyanine, C5-Thiacyanine, C7-Indocyanine, C7-Oxacyanine, CypHer5, Dye-33, cyanines (Cy7, Cy7.5, Cy5.0, Cy5.5, Cy3Cy5 ET, Cy3B, Cy3.0, Cy3.5, Cy2), CBQCA, NIR1, NIR2, NIR3, NIR4, NIR820, SNIR1, SNIR2, SNIR4, Merocyanine 540, Pinacyanol-Iodide, 1,1-Diethyl-4,4-carbocyanine iodide, Stains All, Dye-1041, or Dye-304.

Cyanine dyes are particularly preferred organic dyes for use in the nanobiosensors. All cyanine dyes have an excitation maximum, which is blue shifted by 20-25 nm with respect to their emission maximum (typical for fluorescent singlet states). Exemplary emission spectra of: NS-Cy3.0 ($\lambda$ex=538, $\lambda$em=560), NS-Cy5.5 ($\lambda$ex=639, $\lambda$em=660), NS-Cy7.0 ($\lambda$ex=740, $\lambda$em=760) and NS-Cy7.5 ($\lambda$ex=808, $\lambda$em=830).

Suitable inorganic dyes are selected from the group consisting of metalated and non-metalated porphyrins, phthalocyanines, chlorins (e.g., chlorophyll A and B), and metalated chromophores. Preferred porphyrins are selected from the group consisting of tetra carboxy-phenyl-porphyrin (TCPP) and Zn-TCPP. Preferred metalated chromophores are selected from the group consisting of ruthenium polypyridyl complexes, osmium polypyridyl complexes, rhodium polypyridyl complexes, 3-(1-methylbenzoimidazol-2-yl)-7-(diethylamino)-coumarin complexes of iridium(III), and 3-(benzothiazol-2-yl)-7-(diethylamino)-coumarin complexes with iridium(III).

Suitable fluorophores and phosphophores are selected from the group consisting of phosphorescent dyes, fluoresceines, rhodamines (e.g., rhodamine B, rhodamine 6G), and anthracenes (e.g., 9-cyanoanthracene, 9,10-diphenylanthracene, 1-Chloro-9,10-bis(phenyl-ethynyl)anthracene).

The pI tag(s) are used to modify the normal isoelectric point (pI) of the reporter molecule to permit complete separation from one another so that a plurality of analytes can be targeted in the assay without overlapping. Thus, depending upon the technique used for detection of the nanobiosensor, one or more pI tags may be used. For example, when an electrophoresis-based approach is used, it may be desirable to increase, decrease, or adjust the spacing of the designated (or expected) detection location for each nanobiosensor along the microfluidics channel in the detection chamber (as discussed in more detail below). The nanobiosensors themselves can be designed and calibrated with the detection device, such that each type of nanobiosensor for a particular target analyte has a designated (or expected) position in the detection chamber for each of its reacted and unreacted sensing molecules. For example, the reporter molecules will each have a standard position in the detection chamber where each respective (expected) isoelectric point is reached for the given pH used in the channel. In some cases, reporter molecules comprising different recognition sequences (thus, targeting different analytes) may nonetheless have similar isoelectric points (in reacted and/or unreacted states), resulting in overlapping standard positions along the chamber. Therefore, one or more pI tags can be added to the reporter molecule to adjust the isoelectric point of a given reporter molecule and accordingly adjust the designated location of detection for that particular reporter molecule in the detection chamber, so that the presence of one reporter molecule (and thus one analyte) can be differentiated from the presence another type of reporter molecule (and thus another analyte). Thus, it will be appreciated that the invention allows for separation of the sample into a linearly spaced array of reporter molecules with detectable labels, that will be present (or absent) at designated locations along the channel, and can be "read" similar to a linear barcode. In one or more embodiments, at least 20 different reporter molecules (or bands) can be detected at a time (i.e., in a single assay), and preferably from about 20 to about 100 different reporter molecules (or bands) can be detected at a time (i.e., in a single assay) with a single detector/sensor (e.g., positioned behind the laser or other light source).

Exemplary reporter molecules are listed in Table 2 below, along with their target analyte.

TABLE 2

| Enzyme | Total Sequence | PI | SEQ ID NO: |
|---|---|---|---|
| ALK | Fl-[A]RDIY*AAPFFRKC | 9.31/8.35 | 65 |
| AURKB | Fl-[DD]AMERRRT*SAARRSYC | 9.49/8.56 | 66 |
| CDK2 | Fl-I[C]KARAAVS*PQKRKAD[D]C | 9.68/7.51 | 67 |
| PKD2 | Fl-[DDC]RARKRRLS*APPLASGDC | 8.95/7.72 | 68 |
| MAPK1 | Fl-AKAGPPLS*PRPPHVHC | 6.91/5.63 | 69 |
| JAK 2 | Fl-DLFIPDNY*LKMKPAPC | 5.95/4.46 | 70 |
| P1K1 | Fl-AELDPEDS*MDMDMAPC | 3.25/3.08 | 71 |
| P1K3 | Fl-EDEAEELS*DEDEELKC | 3.65/3.38 | 72 |
| ERK1 | Fl-AAGPAPLS*PVPPVVHC | 6.73/5.50 | 73 |
| JunK2 | Fl'-[D]ASRPPPLS*PLPSPRAC | 7.24/6.11 | 74 |
| MMP 1 | Fl-<u>GAGC</u>[DSD]GPEG-LRGA[R]<u>G</u> | 4.66/3.52 | 75 |
|  | Fl-H$_6$CGPEG-LRGAE$_4$ | 6.2 | 76 |
|  | Fl-H$_6$CGPEG | 7.14 | 77 |
| MMP 2 | Fl'-[H]<u>GAGC</u>GPSA-LVSDG | 3.94/4.31 | 78 |
| MMP 3 | Fl-[H]<u>GAGC</u>GPAG-LRGLG | 7.42/5.01 | 79 |
|  | Fl-H$_6$RCGPAG-LRGLE$_4$ | 6.79 | 80 |
|  | Fl-H$_6$RCGPAG | 8.31 | 81 |

TABLE 2-continued

| Enzyme | Total Sequence | PI | SEQ ID NO: |
|---|---|---|---|
| MMP 7 | Fl-<u>GAGCR</u>VPLS-LTMG<u>DDG</u> | 4.18/8.15 | 82 |
|  | Fl-H$_6$RHRCVPLS-LTMGE2 | 7.66 | 83 |
|  | Fl-H$_6$RHRCVPLS | 10.0 | 84 |
| MMP 9 | Fl'-<u>GAGC</u>HHHVPLS-LYS<u>GDG</u> | 5.14/6.21 | 85 |
|  | Fl-H$_6$E$_3$CVPLS-LYSGK3 | 7.61 | 86 |
|  | Fl-H$_6$E$_3$CVPLS | 6.48 | 87 |
| MMP11 | Fl-H$_6$CKCGA2N-LVRG | 9.64 | 88 |
|  | Fl-H$_6$CKCGA2N | 8.12 | 89 |
| MMP13 | Fl-H$_6$E$_5$CGPQGLA-GQRGIVE2 | 6.13 | 90 |
|  | Fl-H$_6$E$_5$CGPQGLA | 5.88 | 91 |
| MMP14 | FL-H$_6$CDECGPAG-LRLA | 7.09 | 92 |
|  | FL-H$_6$CDECGPAG | 6.77 | 93 |
| CTS B | Fl-<u>GAGCR</u>HGLAG-LAGA<u>HHC</u> | 7.96/8.26 | 94 |
|  | Fl-H$_6$CEDCSL$_2$RSR-MVPNFNC$_2$ | 7.47 | 95 |
|  | Fl-H$_6$RCSL$_2$RSR | 7.56 | 96 |
| CTS D | Fl-<u>GAGC</u>LEVL-FVLGG | 6.38/5.73 | 97 |
|  | Fl-H$_6$KEKCSL$_2$IFR-SWANFNK | 9.72 | 98 |
|  | Fl-H$_6$KEKCSL$_2$IFR | 9.26 | 99 |
| CTS E | Fl'-<u>GAGC</u>HKHKEVVL-VALA<u>RHG</u> | 7.61/6.56 | 100 |
| CTS K | Fl-<u>GAGC</u>HKRKRGLE-GADD<u>RHG</u> | 9.17/9.96 | 101 |
|  | Fl-H$_6$D$_7$CGPRAGR-R | 6.23 | 102 |
|  | Fl-H$_6$D$_7$CGPR | 5.90 | 103 |
| CTS L | Fl-<u>GAGC</u>RRRRELLG-SPPD[D]<u>G</u> | 5.38/8.82 | 104 |
|  | Fl-H$_6$E$_7$CSGV$_2$IA-TVIVITK | 5.50 | 105 |
|  | Fl-H$_6$E$_7$CSGV$_2$IA | 5.08 | 106 |

Fl: Fluorophore;
Fl': mono-sulfonated fluorophore;
*: phosphorylated residue;
Underlined residues: spacer;
Residue(s) in brackets: amino acids added to change pI;
bold C: cysteine to link to magnetic nanoparticles;
ALK: Anaplastic lymphoma kinase;
AURKB: Aurora kinase B;
CDK2: Cylin-dependent kinase 2;
PKD2: Pyruvate dehydrogenase (acetyl transferring) kinase;
MAPK1: Mitogen activated protein kinase 1;
JAK 2: Janus kinase 2;
PlK1: Polo-like kinase 1;
PlK3: Polo-like kinase 3;
ERK 1: extracellular signal-regulated kinase 1;
JunK2: c-Jun N-terminal kinase 2

The reporter molecule can be attached to the nanoparticle via a terminal end of the reporter molecule sequence, or alternatively at a position intermediate to either end of the sequence along the backbone. The detectable label is preferably attached on a terminal end (e.g., N-terminus) of the reporter molecule. For example, the N-terminus of the pI tag nearest the release unit can be labeled with a fluorophore.

Microfluidics Device

Embodiments of the invention are directed to a device for performing the analysis of biospecimens/biological samples using the nanobiosensors. The nanobiosensors are particularly suited for use with microfluidic devices. The microfluidic devices generally comprise a planar substrate comprising a sample inlet well positioned above a sample application region in or on the substrate and at least one detection region in fluid communication with the sample application region via a microfluidic channel extending from the sample application region to the detection region. A washing region may be positioned along the channel intermediate to the sample application region and the detection region. One or more side channels may also be formed in the device to facilitate introduction or removal of components, reagents, buffers, etc. from the main channel. For example, one or more inlet side channels can be formed to introduce a wash buffer into the wash region. Likewise, one more outlet side channels can be formed to remove waste material from the wash region. Similarly, one or more inlet channels may be formed adjacent the detection region to introduce reagents into the detection region and/or to supply electrical connection to the detection region to assist in the separation of the reporter substrates (through, for example, channels containing anolyte and catholyte for isoelectric focusing). The microfluidics channel regions may be separated by one or more valves. One or more valves (e.g., air or mechanical valves) may also be incorporated into the channel to provide forward and/or back pressure. However, as will be appreciated from the additional information below, microfluidics devices in accordance with the invention do not require a pump to move the sample through the channel.

An exemplary device is shown in FIG. 1A-FIG. 1D (side view) and FIG. 2 (schematic top view), and its features and operation are described below. Device 10 generally comprises sample chamber 20, washing chamber 30, and detection chamber 40 positioned in fluid communication along a microfluidic channel 60. Device 10 further comprises a magnet 80 positioned on a translatable stage below channel 60 and configured to mix nanobiosensors 90 and a biological sample within sample chamber 20 and/or to translate nanobiosensors 90 into the various chambers along microfluidic channel 60. In certain embodiments, device 10 further comprises one or more valves 70 interposed within microfluidic channel 60. The operation of device 10 and its individual components may be manual or automated. The separate chambers can be separated from each other using one or more valves 70a-d. Any of a variety of types of valves can be used, so long as they are capable of being opened/closed to allow/prevent nanobiosensors 90 to be moved from one chamber to another. In certain embodiments, the valves are soft lithographic valves. Other exemplary valves include mechanical push-down valves or pinch valves.

Microfluidic channel 60 is generally provided as a central/main elongated void region cooperatively defined by opposing side walls, bottom wall, and optional opposing top wall. Microfluidic channel 60 has a channel length extending generally from the sample chamber 20 to the terminal end of the detecting chamber 40, and a channel width extending between the opposing sidewalls. The microfluidic channel 60 is generally linear, as shown in FIG. 2. However, in certain embodiments, microfluidic channel 60 may be non-linear, branched, or have a variety of other geometries. Microfluidic channel 60 may be a variety of sizes. In certain embodiments, channel 60 has a total channel length (i.e., the distance from sample chamber 20 to the terminal end of detection chamber 40) of less than about 10 cm, preferably less than about 5 cm, and more preferably, less than about 3 cm. In certain embodiments, channel 60 has a total length of from about 1 cm to about 10 cm, preferably from about 2 cm to about 5 cm. In certain embodiments, channel 60 has an average width along its length of less than about 1000 µm, preferably less than about 600 µm, and more preferably less than about 400 µm. In certain embodiments, channel 60 has an average width along its length of about 10 µm to about 1000 µm, preferably about 50 µm to about 800 µm, and more preferably 100 µm to about 500 µm. In certain embodiments, channel 60 has an average height (depth, as measured from the bottom wall to the top of the sidewall) along its length of less than about 200 µm, preferably less than about 100 µm, and more preferably less than about 50 µm. In certain embodiments, channel 60 has an average height (depth) along its length of about 5 µm to about 75 µm, preferably about 10 µm to about 40 µm, and more preferably about 15 µm to about 30 µm.

Device 10 may be manufactured using a variety of techniques and materials. In certain embodiments, device 10 is fabricated from polydimethylsiloxane (PDMS), or other suitable material, on a glass slide or silicon substrate. The materials may be treated to render it hydrophilic. Microfluidic channel 60 may be formed in device 10 using a variety of techniques. In a particularly preferred embodiment, microfluidic channel 60 is formed in device 10 using soft lithography or 3D printing to create the shaped channel. For example, a mold for the PDMS channels can be patterned using a mask and an appropriate light source. The mold may be created using a negative tone photoresist (e.g. SU-8). The negative tone photoresist in the exposed regions is cross-linked and the photoresist in the unexposed regions can be rinsed away using an organic liquid. This results in a mold against which the PDMS prepolymer can be cast. Once the PDMS has crosslinked, it can be peeled from the mask and annealed against a glass or silicon surface. Alternatively, the channels can be etched in glass using well known state of the art techniques and then be sealed with a flat piece of PDMS or a piece of PDMS that contains channels that can connect various channels in the glass. Methods of forming microfluidics channels are known in the art, and include, without limitation, wax printing, wet or dry etching, thermoforming techniques such as hot/roll embossing and injection molding, polymer casting, and direct writing with micro machines or lasers.

Sample chamber 20 comprises an opening 22 and a reservoir or well 24 configured for receiving a biological sample. Sample chamber 20 is in fluid communication with washing chamber 30 via one or more optional valves 70. Washing chamber 30 may include an optional wash inlet 32, as shown in FIG. 2 for introducing a wash fluid, as well as an outlet for waste 34. Washing chamber 30 is in fluid communication via one or more optional valves 70 with detection chamber 40.

In one or more embodiments, detection chamber 40 is particularly configured for microfluidic Isoelectric Focusing (IEF). In one aspect, IEF chamber 40 generally comprises ampholyte reservoir 42, catholyte reservoir 44, anolyte reservoir 46, and pressure fill inlet 48. Ampholyte reservoir 42 is configured to introduce a high-resolution ampholyte mixture into IEF chamber 40. An exemplary commercially-available ampholyte is 39878 SIGMA by Sigma-Aldrich. As shown in FIG. 2, Valve 70c is positioned so as to allow the ampholyte mixture to flow into IEF chamber 40 when opened and prevent the flow of the ampholyte mixture when closed. Catholyte reservoir 44 comprises a catholyte solution, such as a sodium hydroxide solution. Anolyte reservoir 46 comprises an anolyte solution, such as a phosphoric acid solution. An electric field can be applied to IEF chamber 40 by supplying a current to electrodes 50. Additional components necessary for the IEF process (e.g., pI standards, electroosmotic flow (EOF) suppressor, reducing agent, and/or sacrificial ampholytes) can be supplied to IEF chamber 40 via pressure fill inlet 48, which may further comprise valve 70d.

In use, from about 0.1 mL to about 5 mL of biological sample (preferably from about 0.5 mL to about 5 mL and even more preferably from about 1 mL to about 5 mL) can be loaded into the sample chamber 20 reservoir or well 24, along with a plurality of nanobiosensors 90. Exemplary biological samples include, for example, blood, serum, saliva, sputum, or lung fluid (i.e., breath condensate), urine, sweat, and other bodily secretions. In one or more embodiments, the biological sample is not pre-treated, purified, concentrated or otherwise modified prior to mixing with nanobiosensors 90 or adding to sample chamber 20. Nanobiosensors 90 and the biological sample may be added to sample chamber 20 individually or pre-mixed prior to being added to sample chamber 20. The mixture comprising the biological sample and nanoparticles 90 is then incubated. Incubation times can vary depending upon the nanobiosensor and the target analyte, for example from about 1 second to about 1 hour, and preferably from about 1 minute to about 5 minutes. Incubation preferably occurs under ambient conditions (e.g., room temperature, ~27° C.), but can occur at elevated temperatures of from about 28° C. to about 50° C.

Figure 2:
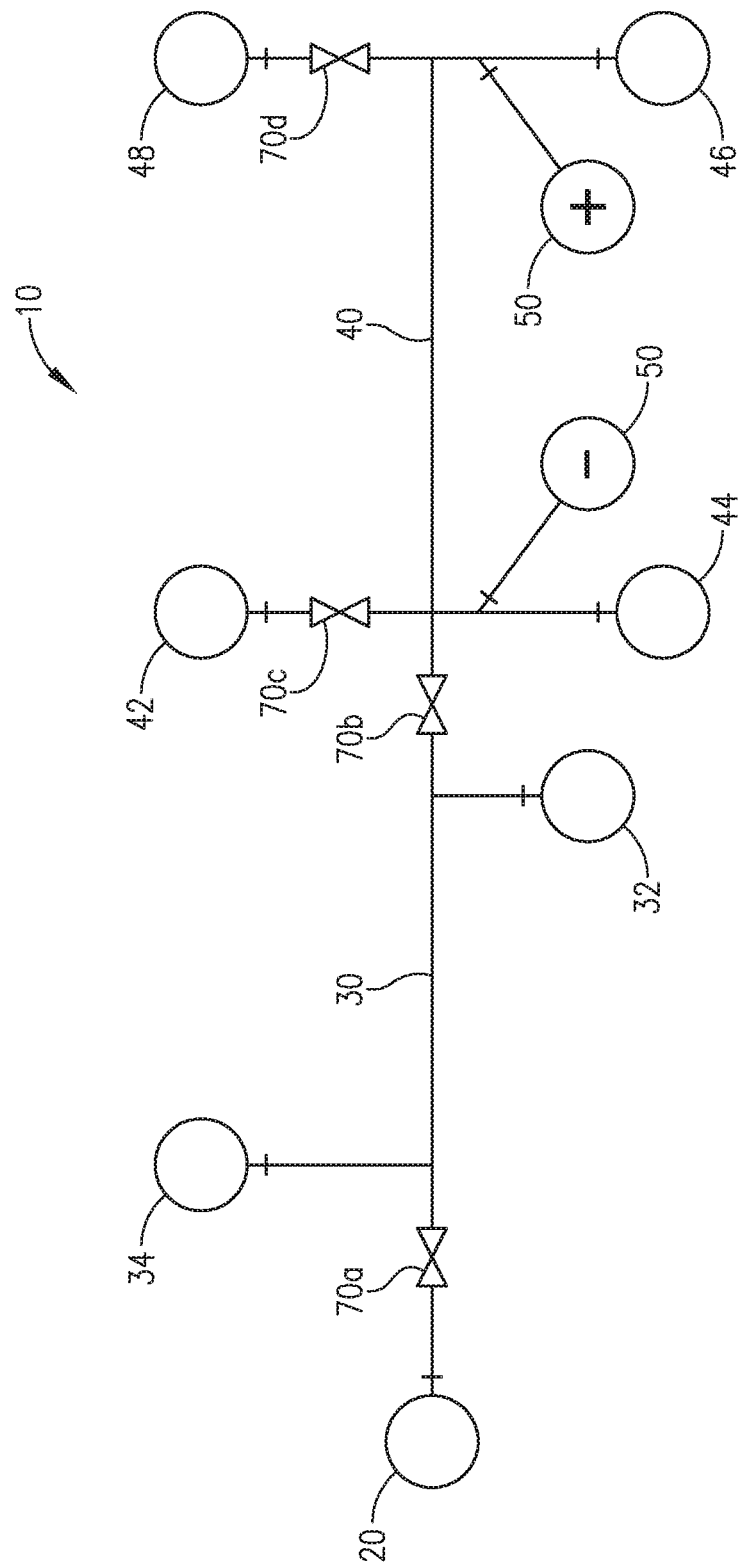
FIG. 2 is a schematic top view of the microfluidic device of FIG. 1.

In one or more embodiments, magnet 80 is initially position below sample chamber 20, as shown in FIG. 1A. From this position, magnet 80 can be rotated manually or automatically by varying an external magnetic field to mix nanobiosensors 90 and the biological sample within sample chamber 20. Magnet 80 may be any kind of magnet, so long as it is capable of moving nanobiosensors 90 within sample chamber 20 and along channel 60, as described herein. In certain embodiments, magnet 80 is a rare-earth magnet comprising an alloy of elements selected from the group consisting of lanthanides, scandium, yttrium, and mixtures thereof.

Figure 1B:
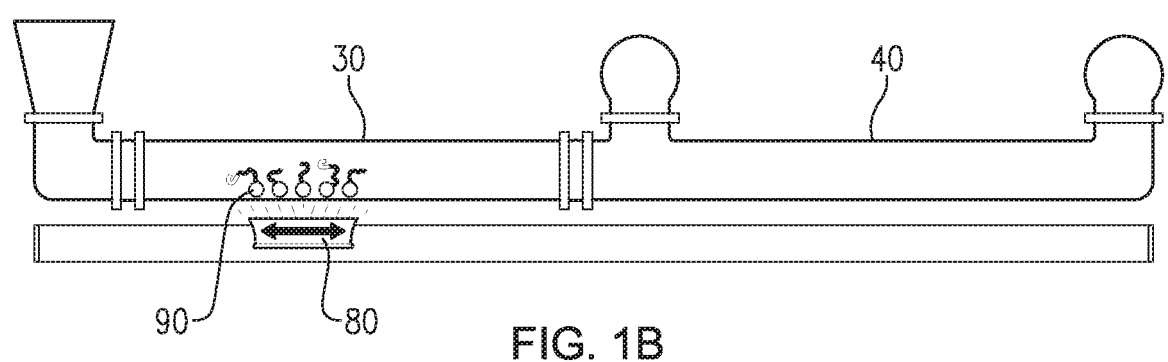
FIG. 1B is a schematic side view of a microfluidic device in use accordance with one embodiment of the present invention.
Figure 1C:
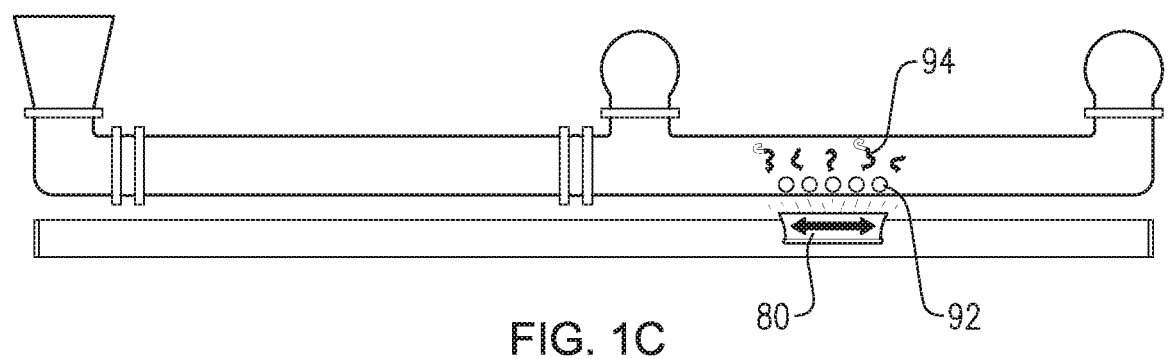
FIG. 1C is a schematic side view of a microfluidic device in use accordance with one embodiment of the present invention.

After incubation, nanobiosensors 90 are transferred to washing chamber 30 by laterally translating (e.g., sliding) magnet 80 from below sample chamber 20 to a position below washing chamber 30, as shown in FIG. 1B. The magnetic attraction between magnet 80 and nanobiosensors 90 causes the nanobiosensors 90 to move along the microfluidic channel 60 from sample chamber 20 to washing chamber 30, as the magnet 80 correspondingly moves along a parallel path below the channel 60. In other words, the magnet 80 pulls the nanobiosensors 90 along the channel and/or the nanobiosensors 90 follow the attractive force of the magnet 80. Valve 70a can be opened, while valve 70b remains closed, to allow for easy transfer into washing chamber 30. Once nanobiosensors 90 have been transferred into washing chamber 30, valve 70a can be closed. Nanobiosensors 90 are washed within washing chamber 30 to the biological matrix, which reduces the matrix effects and thus noise during subsequent optical detection steps. In certain embodiments, as shown in FIG. 2, the washing step comprises introducing a wash fluid via wash inlet 32. The wash fluid may be pumped into the main channel 60 through wash inlet 32 so as to mix with nanobiosensors 90 within wash chamber 30, with the waste exiting via waste outlet 34. In one or more embodiments, the wash inlet 32 is positioned at the distal end of the wash chamber 30 (farther from the sample chamber 20), and when the wash fluid is introduced, it travels in a direction from the distal end of the wash chamber 30 towards the sample chamber 20 (i.e., "backwards" or "upstream"), and exits via the waste outlet 34, which is positioned at the proximate end of the wash chamber 30 (closer to the sample chamber 20). In one or more embodiments, the wash fluid comprises de-ionized water or a mixture of de-ionized water and a non-ionic surfactant. The washing step may comprise a single wash or a series of two or more washes. After washing, valve 70b can be opened, and nanobiosensors 90 are transferred into detection chamber 40 using magnet 80, as shown in FIG. 1C. It will be appreciated that the nanobiosensors 90 are moved in a direction of flow that is opposite of the wash fluid direction, from the wash chamber 30 to the detection chamber 40.

Figure 1D:
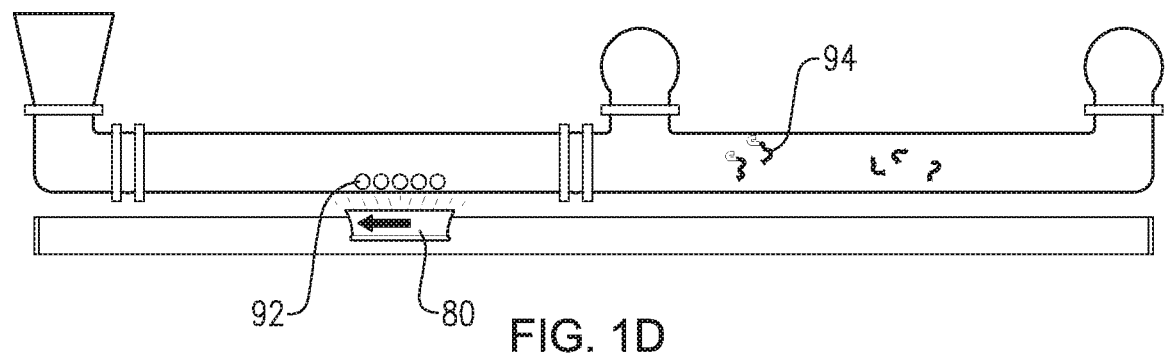
FIG. 1D is a schematic side view of a microfluidic device in use accordance with one embodiment of the present invention.

While magnetic nanoparticles 92 used in the nanobiosensors 90 are useful for mixing and transporting the peptide substrates, they can hinder detection techniques, such as IEF separation, due to their charge and size dispersion, and thus they should be separated from the reporter molecule 94. The release unit 96 allows the reporter molecules 94, both reacted/unreacted, to be delinked from nanoparticles 92 in the nanobiosensors 90 before the detection step is performed. In one or more embodiments, where disulfide release units are used, the disulfide bridges connecting the reporter molecules 94 (both cleaved/modified and uncleaved/unmodified) to the nanoparticles 92 are reduced, thereby releasing the reporter molecules 94 from the nanoparticles 92. Other release mechanisms are described in detail above regarding release unit alternatives. Regardless, once "de-linked," the nanoparticles 92 are then removed from detection chamber 40 by translating the nanoparticles 92 out of the chamber 40, using magnet 80, as shown in FIG. 1D. Using magnet 80, nanoparticles 92 are returned to any of the upstream chambers (e.g., washing chamber 30 or sample chamber 20) or outlets to be cleaned and prepared for re-use in further nanobiosensors 90.

Once nanoparticles 92 are removed from IEF chamber 40, the released peptide substrates 94 are focused into discrete optical bands via IEF. IEF is an analytical technique that is unique compared to most separation methods in that analytes are simultaneously separated and concentrated as they are focused at their pI (isoelectric) points along a pH gradient created through the addition of carrier ampholytes to the separation solution.

To perform IEF, the sample (i.e., the reporter molecules), carrier ampholytes (the pH gradient forming compounds), an electroosmotic flow (EOF) suppressor, and a reducing agent are loaded into the separation column (in this case, the detection chamber 40). Exemplary EOF suppressors include methylcellulose (MC), polyvinylpyrrolidone (PVP, MW 360,000), or hydroxymethylcellulose (HPMC). As shown in FIG. 2, an anolyte (e.g., phosphoric acid) is added to anolyte reservoir 46 and a catholyte (e.g., sodium hydroxide) catholyte reservoir 44. An electric field is applied and the current decreases as the reporter molecules (which may or may not be bound to a target analyte, or have been modified by a target analyte), and ampholytes reach their isoelectric points or points of zero (neutral) charge. Advantageously, IEF in chamber 40 of microfluidic channel 60 can focus the reporter molecules in less than about 30 minutes, preferably less than about 10 minutes, and more preferably less than about 5 minutes. This IEF process is robust and reproducible, and may produce peak capacities of at least about 20 different bands, preferably at least about 50, and more preferably at least about 80. In certain embodiments, the IEF process in accordance with embodiments of the present invention can produce peak capacities of up to about 100 different bands. The IEF process is able to increase concentration of the peaks (focused zones) by at least about 1,000 times, preferably at least about 1,000,000 times. Once focused, the reporter molecule bands are stable for several minutes due to the EOF suppressor being added to the ampholyte. The focused bands may visually resemble a "barcode" within IEF chamber 40, and the bands may be "read" similar to a barcode, as discussed in more detail below.

Once the various peptide substrate bands have been separated and focused within IEF chamber 40, an optical detector can be used to analyze the presence (or absence) of the various reporter molecules within IEF chamber 40. A number of techniques can be used to analyze the resulting peptide bands within IEF chamber 40, including optical detection techniques. Exemplary optical detection techniques are described below. However, it should be understood that other methods of analyzing the peptide bands are also within the scope of the present invention. In general, the methods involve exposing the reporter molecules in the detection chamber (and thus any attached detectable labels) to an appropriate energy source. The wavelength used will depend upon the detectable labels used in the nanobiosensors. Both the position/presence and concentration/intensity of the signal from the detectable label can then be sensed or detected with the appropriate sensing or detecting instrument (examples described below) for both quantitative and qualitative assessment of the reporter molecules. The detector generates an analog signal that is sent to a decoder that interprets the signal, and coverts it into an output that can be read to indicate the results of the assay.

In one embodiment, the imaging and detection is performed using an inverted microscope stage (e.g., Nikon TE-2000U) with a halogen excitation source, a fluorescein filter cube, and a camera (e.g., Princeton Instruments CCD). This embodiment provides flexibility to modify fluorescent tags and imaging areas easily while optimizing the separations. While the entire chamber cannot be imaged with the microscope at one time, the chamber can be scanned by sliding the stage along the length of the chamber (or vice versa). A 2048-element linear CCD line camera (2000:1 S/N ratio, 900 Hz scan rate with a max sensitivity in the 500-600 nm range) can be used to image the IEF results in IEF chamber 40. This embodiment should resolve pH differences as small as $\Delta pH/\#pixels=7/2048=0.0034$ pH units, which is narrower than can be focused using IEF, and thus it should not be the peak resolution limiting factor. The excitation source for the focused fluorescently labeled reporter molecules is a solid-state diode pumped 488 nm laser. The laser line is spread out into an excitation line using a cylindrical lens.

In another embodiment, an organic light emitting diode (OLED) array can be used to spatially scan the IEF chamber by turning on each row of diodes in the chamber sequentially. The emitted light from the focused fluorescently labeled substrate bands is detected using a photomultiplier tube (PMT). The excitation is performed, for example, using a SXGA120-R5 1280×1024 low power monochrome green xlt AMOLED microdisplay from Emagin with a thin fiber optic faceplate, or other similar instrument. The OLED array is positioned below IEF chamber 40. Between chamber 40 and the OLED, a thin excitation filter is positioned. The OLED array can then be manually or automatically driven in a scanning mode along the length of IEF chamber 40, preferably over a period of less than 5 seconds. Rescanning can be performed to improve the signal-to-noise (S/N) ratio, if necessary. The emission from the fluorescently labeled peptide substrates is then measured using a photomultiplier tube (e.g., Hamamatsu R-928 PMT) positioned behind an emission filter. The OLED array has pixel density such that the resolution should be 7/1024=0.0068 pH units, which is which is narrower than can be focused using IEF, and thus it should not be the peak resolution limiting factor. Because the emission from the OLED is 520±55 nm, a more redshifted dye than fluorescein should be used in this embodiment.

Figure 3:
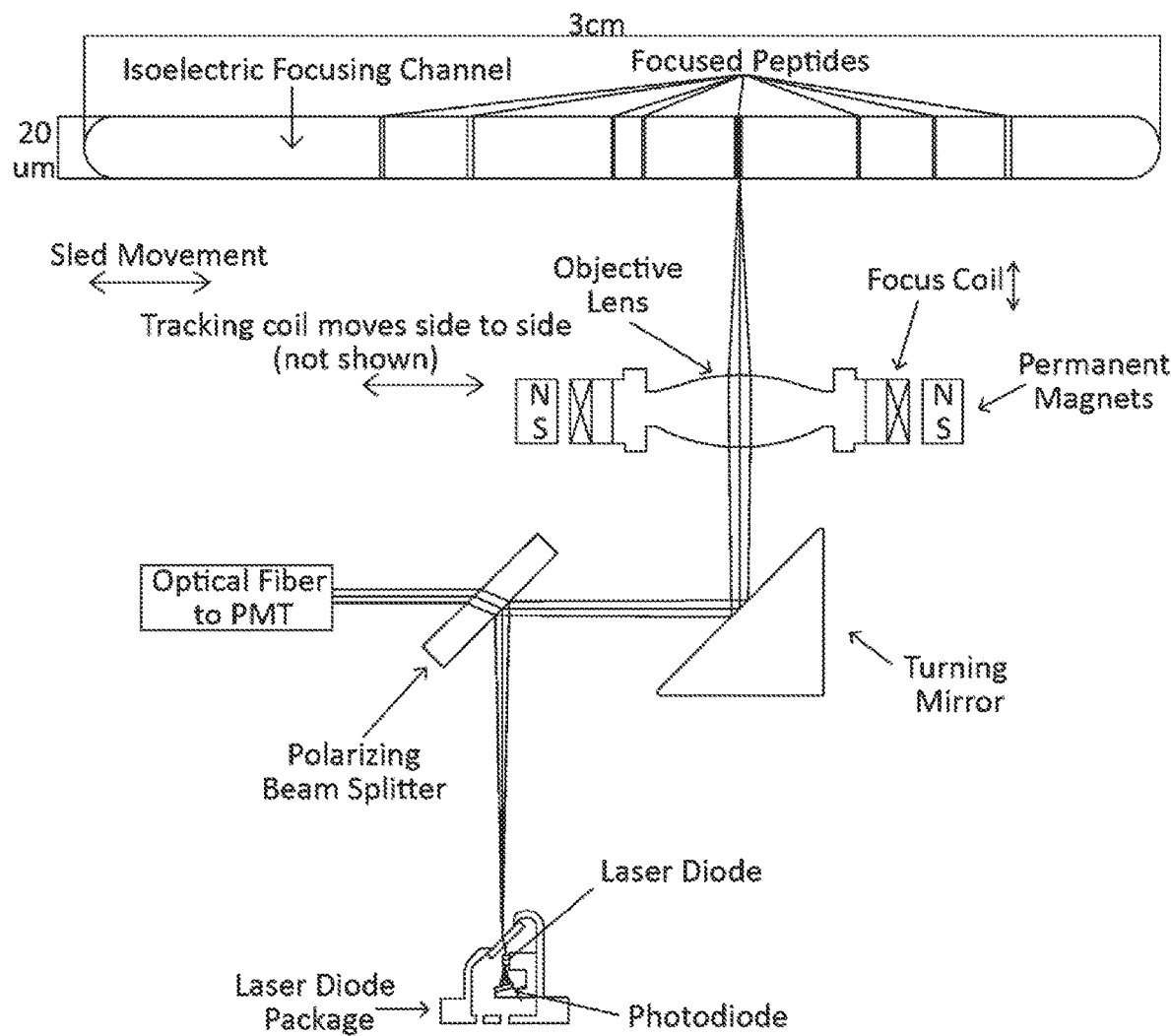
FIG. 3 is a schematic diagram of an optical detector apparatus in accordance with one embodiment of the present invention.

In another embodiment, detection is performed using a digital versatile disc (DVD) optical pickup head and stepper motor that moves the head. A schematic representation of this embodiment is shown in FIG. 3, which includes the laser diode package (laser diode and photodiode) and optics components. In this embodiment, the red (650 nm) diode laser is controlled using a constant current source. The stepper motor can be controlled through an H-bridge, for example, using LabVIEW. The photodiode used for autofocusing and reading the pits in the conventional DVD is removed and replaced by a 100-μm multimodal fiber. The emitted light from the channel is focused onto the surface of the fiber using the optics integrated in the DVD optical pickup head. The fiber then transmits the light to a photocathode (e.g., Hamamatsu microPMT). A cylindrical lens is used to focus the light exiting the fiber onto the rectangular photocathode in the photocathode, and a bandpass (and/or holographic notch) filter is used to filter out the excitation light. The optical fiber serves as the spatial filter. The spatial resolution of the detector is governed either by the laser spot size or the smallest increment that the stepper motor can be moved, both of which are smaller than the most narrowly focused IEF bands in chamber 40.

The device and methods in accordance with embodiments of the present invention have a number of advantages over the prior art. For example, the use of the magnetically translatable nanoparticles in the nanobiosensors allows for a pre-concentration of the peptides prior to the IEF step. Using this pre-concentration, the signal is further enhanced as the concentration of the nanobiosensors are increased $10^6$-fold, for example from a ~1 mL sample volume into a ~nL focused band. One potential issue with IEF is the limited sample volume that can be loaded. For a typical microfluidic IEF device, the volume of sample that can be loaded is defined by the IEF channel/column volume which is usually on the order of ~180 nL (for a 3 cm×300 m×20 m channel). The final focused bands, based on a ~0.05 pH resolution, are ~200 um, giving a preconcentration ratio of about 75 if ½ the initial column volume is loaded with sample. If the nanobiosensors were placed in a 100 nL sample volume with the enzymes present at a concentration of $~10^{-15}$ M, there would only be ~60 enzyme molecules in the analyzed sample. This would be very difficult to detect. For traditional plate readers where the sample volume is ~10-100 μL, the number of enzymes is ~6000-60,000.

By adding the magnetic nanoparticle to the reporter molecules, the nanobiosensor can now be added to a larger initial volume of sample and later removed through the use of a magnet into a much smaller volume to be analyzed. For example, the nanobiosensors could be added to a sample volume of 1 mL and then moved to the IEF region of an integrated microfluidic device. Reducing agents, such as DTT, are often used in IEF and can be added to the ampholyte mixture without affecting the formation of the pH gradient. Under such conditions the disulfide bond is reduced, releasing the uncleaved and cleaved peptide substrates from each particle. Because the final peptide substrate bands will be focused to a volume of ~1 nL that results in a concentration enhancement of ~$10^6$. Because the focused bands are stable, multiple images of the final result can be signal averaged to further improve the LOD.

Additionally, the peak capacity for the IEF chamber can be up to about 80, or even about 100, so a multiplexed sample of at least 20 cleaved/uncleaved or modified/unmodified reporter molecule pairs can be separated. One particular advantage of this technique is that amino acid sequences (pI tags) can be added to the ends of the substrates to alter their pIs so that none of the reporter molecules will overlap after they are focused.

Target analytes that could be detected in embodiments of the invention include protease biomarkers (e.g. matrix metalloproteinases (MMPs), serine proteases, and cysteine proteases), kinase biomarkers (Anaplastic lymphoma kinase (ALK) or CD246 (cluster of differentiation 246), Aurora family of kinases, Cell Cycle Kinases, Cyclin-dependent kinase 2 (CDK2), Protein Kinase D 2 (PKD2), Janus Kinase 2 (JAK2), Polo-Like Kinases, Mitogen-activated protein (MAP) kinases), other enzymes capable of posttranslational modifications, cytokines/chemokines, and the like. The protease biomarkers that are used to validate the exemplary microfluidics device have been shown to be elevated in level 1 stage breast, lung and pancreatic cancers, compared to the levels in apparently healthy human subjects. Thus, embodiments of the present invention are particularly suitable for detecting these markers in spiked commercially available heat-deactivated serum samples and model cell systems at clinically relevant levels for stage 1 and stage 0 detection of cancers.

Figure 4A:
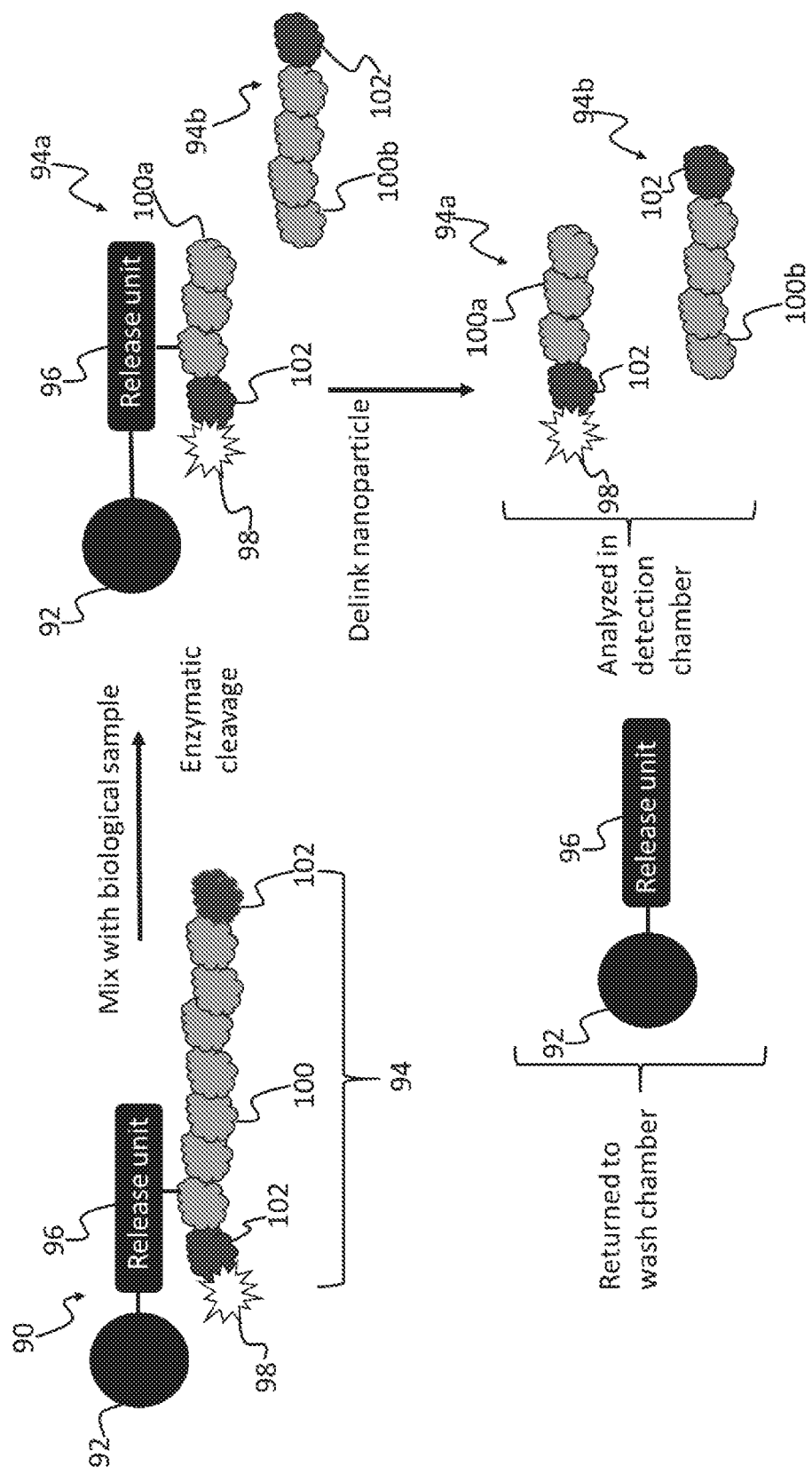
FIG. 4A illustrates a reaction mechanism for a enzymatic cleavage-based nanobiosensors in accordance with embodiments of the present invention.
Figure 4B:
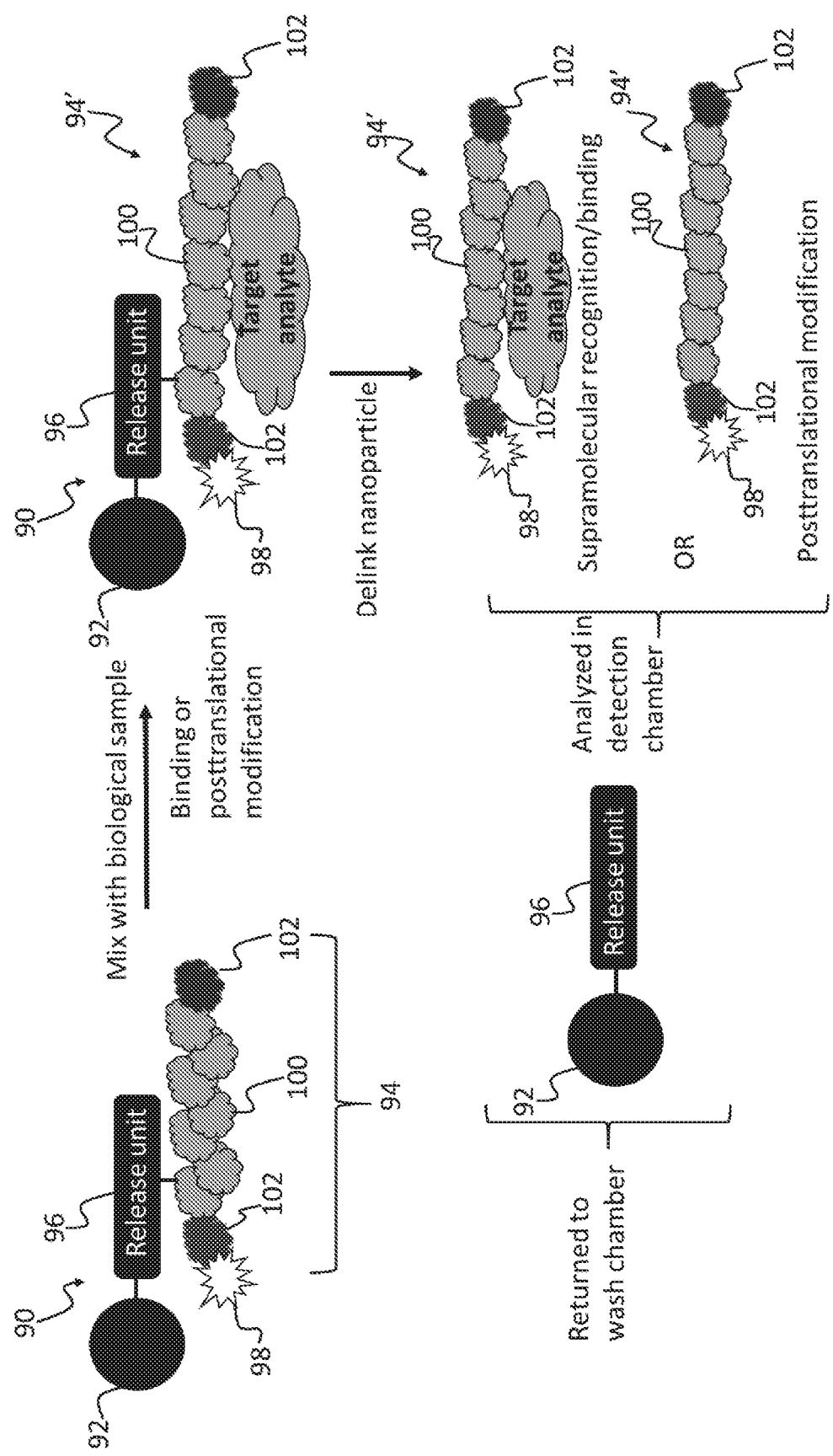
FIG. 4B illustrates a reaction mechanism for posttranslational modification and supramolecular recognition (binding) based nanobiosensors in accordance with embodiments of the present invention.

Exemplary reaction mechanisms of the different types of nanobiosensors 90 are depicted in FIG. 4A and FIG. 4B. As described above, the nanobiosensors 90 comprise a magnetic nanoparticle 92 linked to a reporter molecule 94 by a release unit 96. The reporter molecule comprises a detectable label 98, a recognition sequence 100, and one or more optional pI tag(s) 102. The nanobiosensors 90 will have peptide sequences specific for a particular target analyte (e.g. cathepsin, kinase, matrix metalloprotease (MMP) or other enzyme that catalyzes peptide cleavage or a posttranslational modification). For example, as illustrated in FIG. 4A, if a protease is present and active, it will cleave the sequence at a specific position resulting in two reporter molecule products 94a and 94b with different isoelectric points (pIs). Similarly, as shown in FIG. 4B, if a kinase or other posttranslational enzyme (e.g. arginase) is present, it will biochemically modify its respective oligopeptide leading to a modified reporter molecule product 94', which may or may not include a bound analyte, but nonetheless will have a different pI from the unreacted/unmodified reporter molecule 94. The resulting cleaved or modified reporter molecule can then be detected and correlated with a disease condition based upon its position (i.e., presence of absence) at its designated detection region in the channel.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

Prototype nanobiosensors comprise 5 principal components: a superparamagnetic $Fe/Fe_3O_4$ nanoparticle, a disulfide bridge, reporter molecule containing a protease specific peptide substrate, a fluorophore, and 2 pI tags (FIG. 4A and FIG. 4B). Each pI tag (short peptide sequences), will be positioned on each end of the protease specific peptide substrate. These pI tags will be used to adjust the pI of the uncleaved and cleaved peptide substrates so that they can be completely separated from one another and the other peptide substrates used for the multiplexed analyses. Between one of the pI tags and the enzyme substrate will be a cysteine that can be linked to another cysteine on a superparamagnetic Fe/Fe3O4 nanoparticle through a disulfide bridge (although the cysteine could also be at the end of the sensor followed by the pI tags, the reporter peptide, and 2nd pI tag). The N-terminus of the pI tag nearest the disulfide linkage will also be labeled with a fluorophore.

The pI tags for all of the nanobiosensors and their cleaved counterparts are designed so that they should all be resolved from one another by at least 0.1-0.2 pI units. All consensus sequences are designed based on known cleavage motifs.

Solid-supported peptide synthesis is utilized to prepare the reporter molecules. The fluorescent dye (here: 5-carboxy-fluorescein) is attached while the oligopeptide is still attached to the resin. Wang resins will be utilized, which permits the formation of a carboxylate group at the C-terminal end. The N-terminal end features an amine group after the oligopeptide is cleaved from the Wang resin. Depending on the lengths of the synthesized oligopeptides, the density of oligopeptides on the resin, as well as additional factors (e.g. steric hindrance, formation of beta-sheets etc.), the expected yields range from 95 to 65%. Therefore, the final step of dye-attached oligopeptide synthesis involves purifying the product after cleavage from the resin. Classically, this is achieved with HPLC.

The $Fe/Fe_3O_4$ core/shell nanoparticles are synthesized by thermal decomposition of $Fe(CO)_5$, followed by kinetic growth of the formed iron(0, bcc) nanocrystals. Once they reach a diameter of 35 nm, the Fe(0) nanocrystals are passivated by treating with oxygen, which leads to a strongly adherent $Fe_3O_4$ layer. The latter is subsequently coated with 3,4-Dihydroxyphenylacetic acid to create nanoparticles that can be easily dispersed in various media (aqueous buffers, breath condensate, etc.). After attaching 3-mercaptopropionic acid through an amide bond to the dopamine layer, disulfide bonds between a cysteine group of the fluorescein-attached oligopeptides and the thiol-group of 3-mercapto-propionic amide can be formed. This bond can be reductively cleaved upon addition of THPP (tris-hydroxypropyl-phosphine) to delink the nanoparticles from the reporter molecule.

Example 2

The nanobiosensors are mixed with heat-deactivated serum samples that are "spiked" with commercially available (recombinant) proteases and incubated. This is followed by a wash step and IEF focusing of the multiple nanobiosensors. The initial separation/detection column is fabricated to be 3 cm long and filled with a pH 3-10 range high resolution ampholyte solution (39878 Sigma), dithiothreitol (DTT) or THPP, 0.4% methyl cellulose (MC) to suppress EOF, 1.7 mM iminodiacetic acid, 40 mM arginine, and the peptide substrate sample. After filling the channel, excess mixture is removed from the reservoirs and ~200 mM $H_3PO_4$ added to the anolyte reservoir and ~300 mM NaOH to the catholyte reservoir. Both reservoirs will also contain 2.5% methyl cellulose. Preconditioning is performed by rinsing the channel with 1:1 methanol and 1M sodium hydroxide. After conditioning, the channel is filled with 0.4% methylcellulose and allowed to sit for 10 min to create an EOF reducing coating. The sample is then loaded. The anolyte/catholyte wells/channels are rinsed 2× with ultrapure water then filled with the anolyte and catholyte. 300V is applied for ~5 min to focus the peptides or until the current drops from 25 uA to 2-4 uA. The applied electric field is optimized to minimize the focusing time and maximize resolution. The effectiveness of the different suppressors at various concentrations to suppress EOF is evaluated. The drift should be <0.05 pH units over the course of the detector scan time (at present this is about 30s). A peak capacity of 80 is the goal. Additionally, the resolution is maximized through adjustments to the ampholyte and reducing agent (e.g., THPP) concentrations using in-house synthesized fluorescently labeled pI standards that have been calibrated against standard uv calibration standards in a cIEF system. Our initial experiments with a scanning bench scale device indicate that it can be cleaned, pretreated, and reused dozens of times.

Example 3

Materials. The following chemicals were obtained from commercial sources: Tris(hydroxypropyl)phosphine (THPP), Methyl Cellulose, and Ampholyte high resolution, pH 3.0-10.0, were purchased from Sigma Aldrich (St. Louis, Mo.). Thermo Scientific™ Pierce™ MS Grade Trypsin Protease, Acetonitrile (HPLC Grade), Trifluoroacetic Acid, Glacial Acetic Acid, Calcium Chloride, Phosphoric Acid, Sodium Hydroxide, and Brij 35 (Enzymatic Grade), were purchased from Fisher Scientific (Waltham, Mass.). 1.5M Tris-HCl, pH 8 was purchased from BioRad (Hercules, Calif.). DL Arginine was purchased from Acros Organics (Geel, Belgium).

Methods.

Trypsin Digestion. 50 mM Tris-HCl (pH 7.8), 1 mM $CaCl_2$, 0.005 mg/mL Trypsin, and 0.1 mg/mL Trypsin Substrate were mixed and then incubated at 37° C. with samples taken for analysis at 0hr, 2 hr, and 24 hr. The digestion was stopped by adding acetic acid to adjust the pH below 4.

Figure 5:
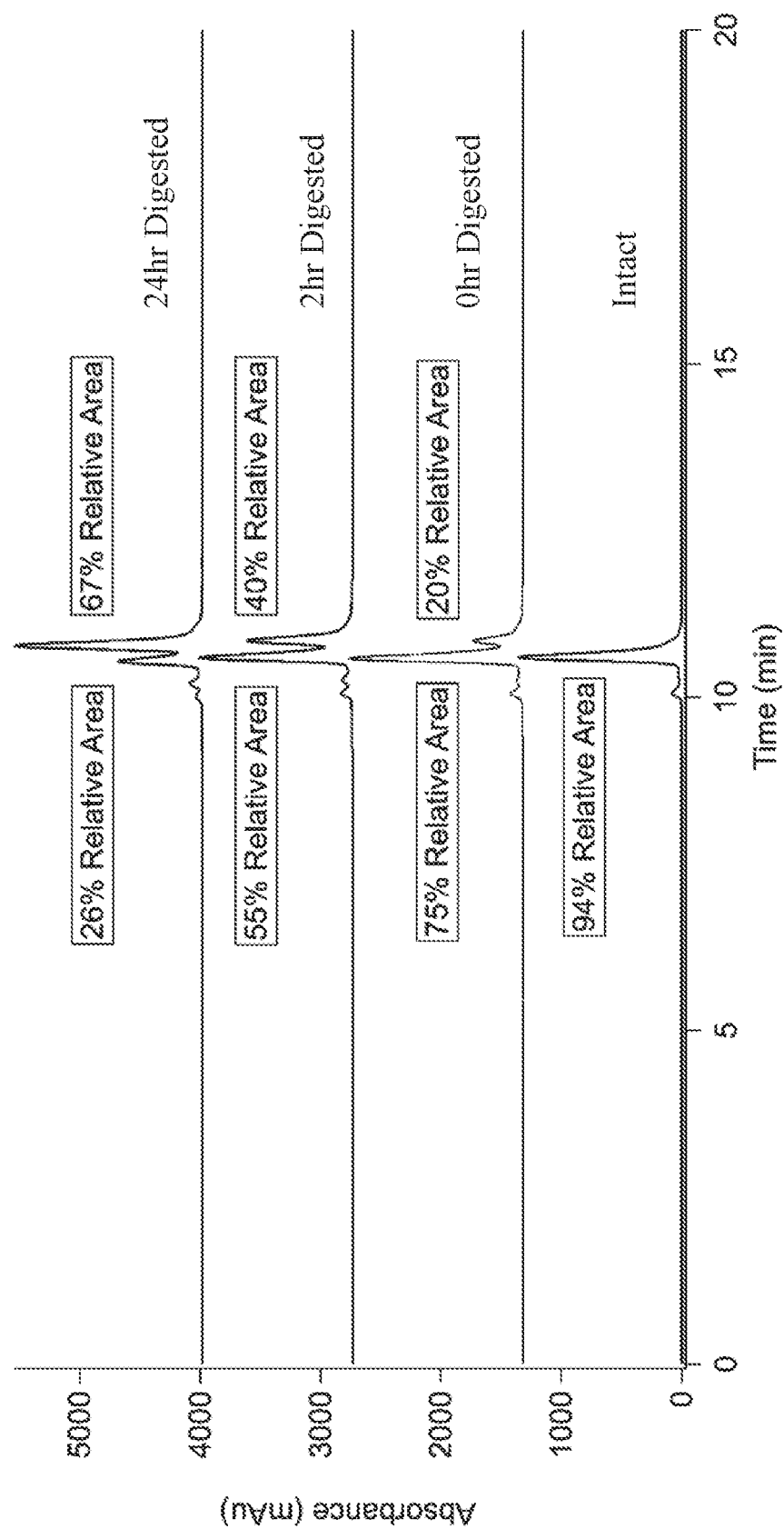
FIG. 5 is a graph showing HPLC results following trypsin digestion at different time periods.

HPLC Testing. The digestions were tested on a Thermo Fisher Ultimate 3000 with a Variable Wavelength Detector and an Acclaim 300 C18 column. The parameters were 0.3 mL/min flow rate, with a gradient of 5% acetonitrile to 80% over 15 min and a 5 min hold at 80%. The data was analyzed with Igor Pro (WaveMetrics Inc., Lake Oswego, Oreg.). The results are shown in FIG. 5.

Figure 6:
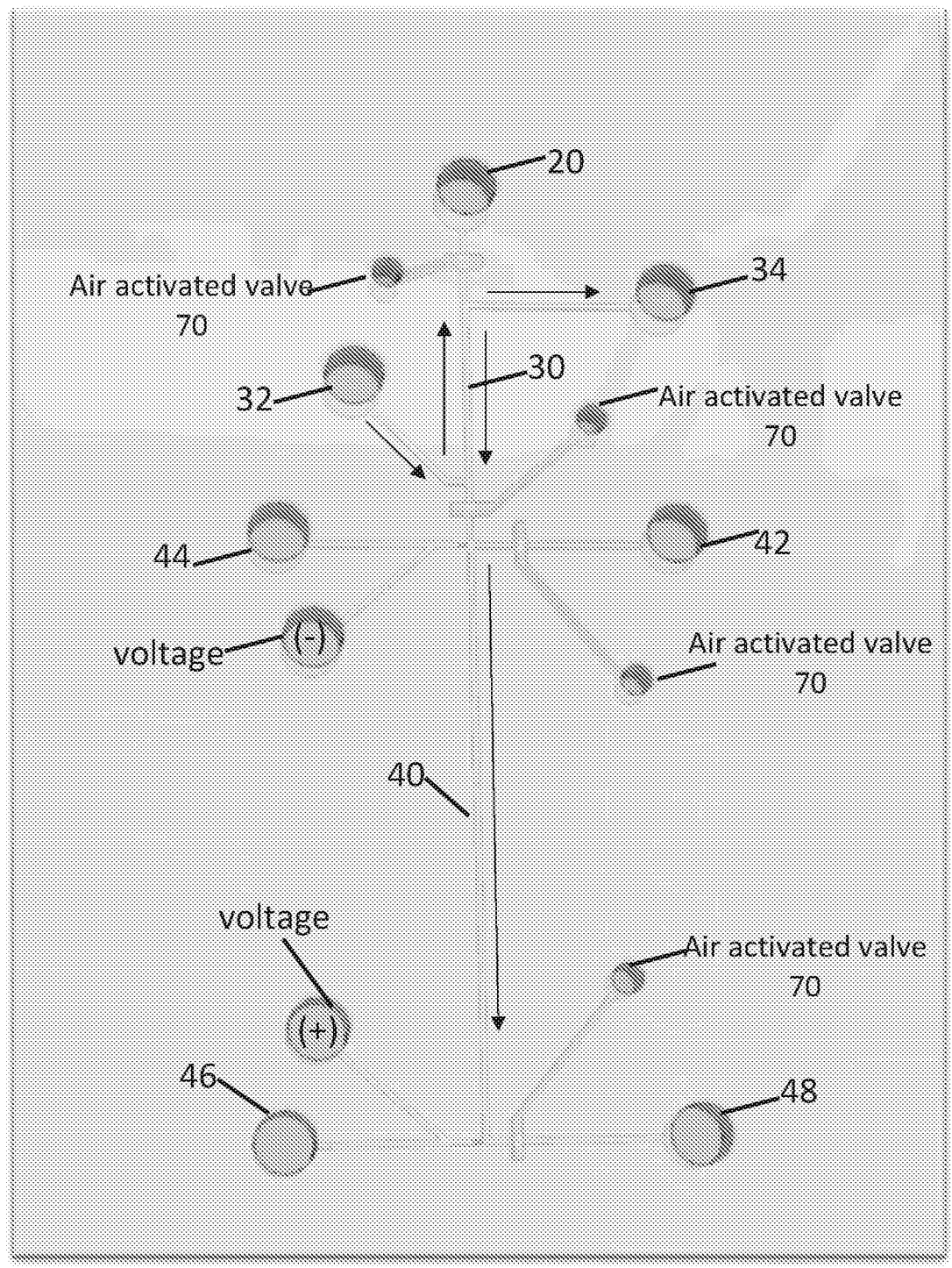
FIG. 6 is an annotated photograph of a microfluidic device fabricated in Example 3.

Fabrication of PDMS Microfluidic Isoelectric Focusing Device. Soft photolithography was used to create the desired channel pattern, by using a positive photoresist on a Si-wafer substrate. PDMS prepolymer and curing agent (Sylgard 184, Dow Corning Inc., Midland, Mich.) were uniformly mixed at a ratio of 10:1, respectively, and degassed for 30 min under vacuum. The PDMS was poured into a mold on Si wafer that contained the channel pattern. The PDMS was cured in an 80° C. oven for 90 minutes. At the end of the curing process, the PDMS was carefully peeled from the glass substrate to become the bottom layer of the microchip. The reservoirs were created with a 3 mm biopsy punch and then the channel layer was sealed to a glass slide. The microchannel was 3 cm in long, 300 μm wide, and 16 μm deep. A photograph of the device is shown in FIG. 6.

Isoelectric Focusing Testing. The digestions were also tested on the created device. The channel was cleaned with 50% 1M NaOH+50% Methanol for 10 min. Then the channel was pretreated with the 0.4% methyl cellulose for 30 min. The sample consisted of: 40 mM Arginine (High pI Sacrificial Ampholyte), 0.05% Acetic Acid (Low pI Sacrificial Ampholyte), 0.11% Brij 35 (Surfactant), ~1-100 μM Rhodamine Tagged Peptide (Sample), 1% Carrier Ampholytes, and 0.4% Methyl Cellulose (EOF Suppressor).

Figure 7:
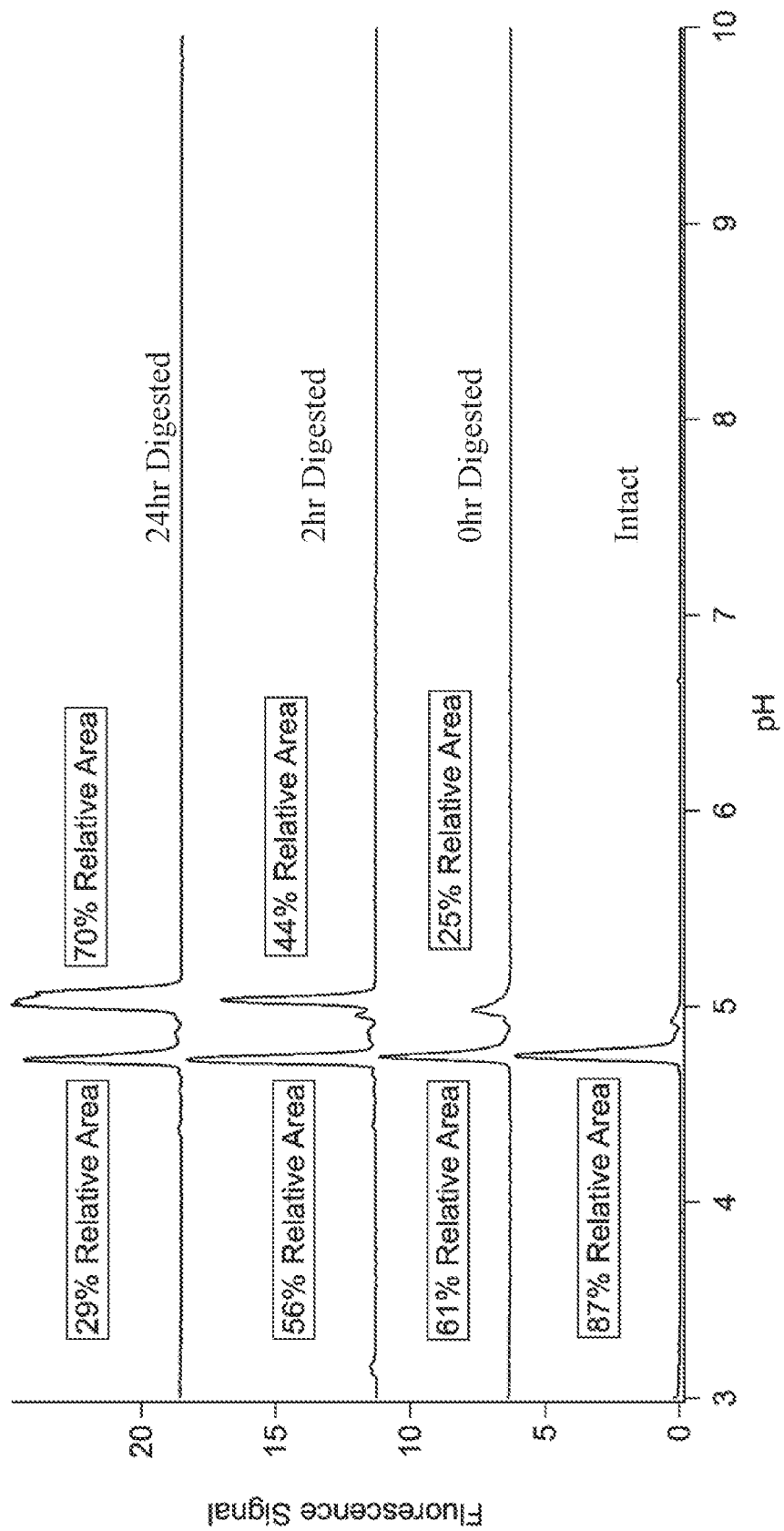
FIG. 7 is a graph showing isoelectric focusing results following trypsin digestion at different time periods.

The sample was loaded into the channel and then the reservoirs were filled with the anolyte (200 mM $H_3PO_4$+2% methyl cellulose) and catholyte (300 mM NaOH+2% methyl cellulose). The microfluidic chip was then aligned on the detector and the voltage was applied (200V/cm) until the current dropped to 10% of its initial value. While this was occurring, the channel was automatically scanned at 937 μm per second over the detection point and the fluorescence was detected using a μPMT (Hamamatsu Photonics, Japan). LabView (National Instruments, Austin, Tex.) programming was used to automatically control all motion, voltage, data collection, and saving. Data was analyzed using Igor Pro. The results are shown in FIG. 7.

Nanobiosensor Peptide Reduction Testing. 50 mM Tris-HCl buffer @ pH=8 was mixed with THPP for a 1.3 mM THPP solution. The nanoparticles were resuspended by swirling and then 50 uL were removed into a 1.5 mL tube. A neodymium magnet was used to pull the particles to the side and remove the supernatant. The 1 mL of 1.3 mM THPP in 50 mM Tris-HCl @pH 8 was added and then mixed and then placed on a rotator for 30 min. After 30 min the nanoparticles were pulled to the side by the magnet and then 100 μL of the sample was removed for testing in the IEF microfluidic chip.

Figure 8:
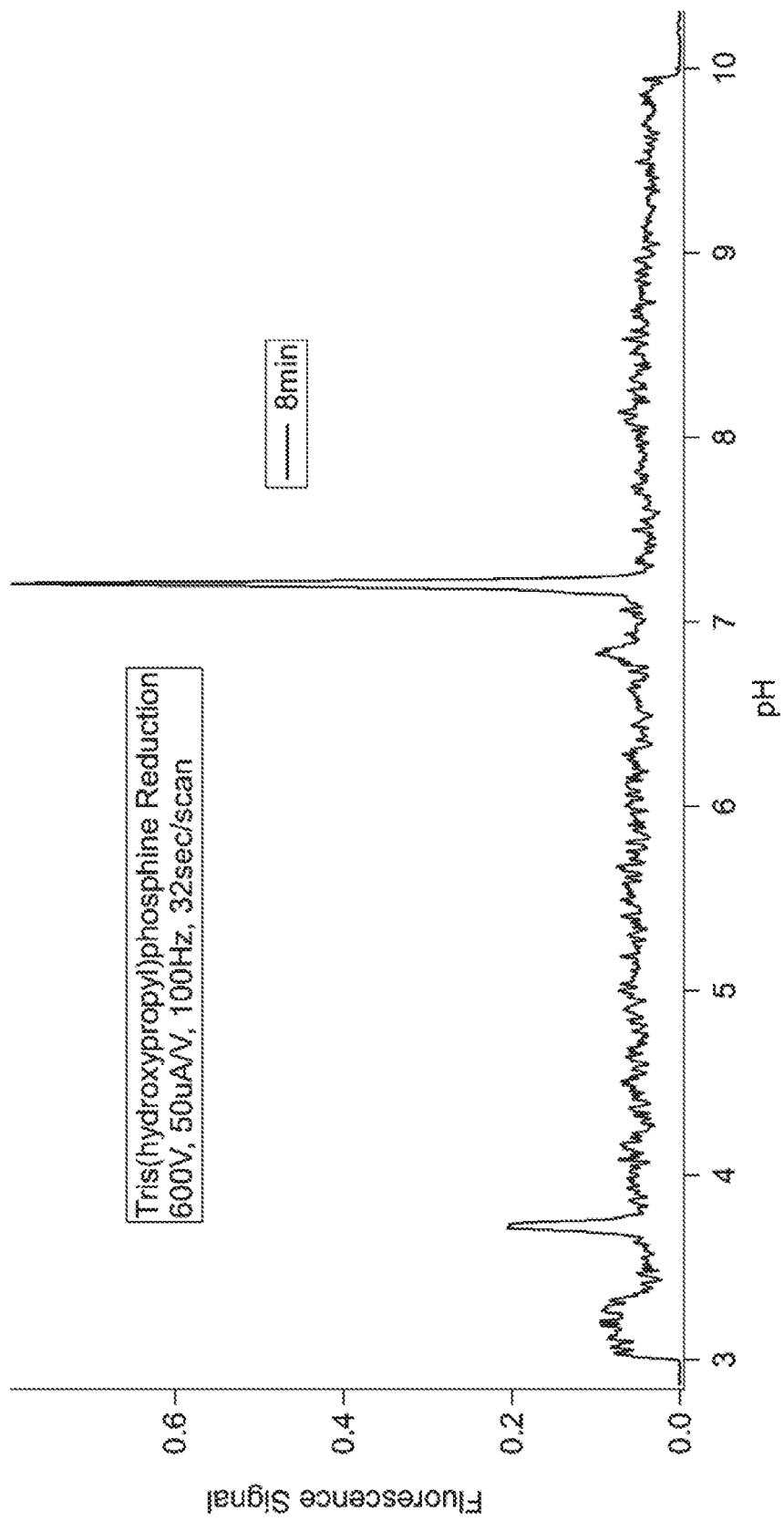
FIG. 8 is a graph showing isoelectric focusing results following disulfide reduction.
Figure 9:
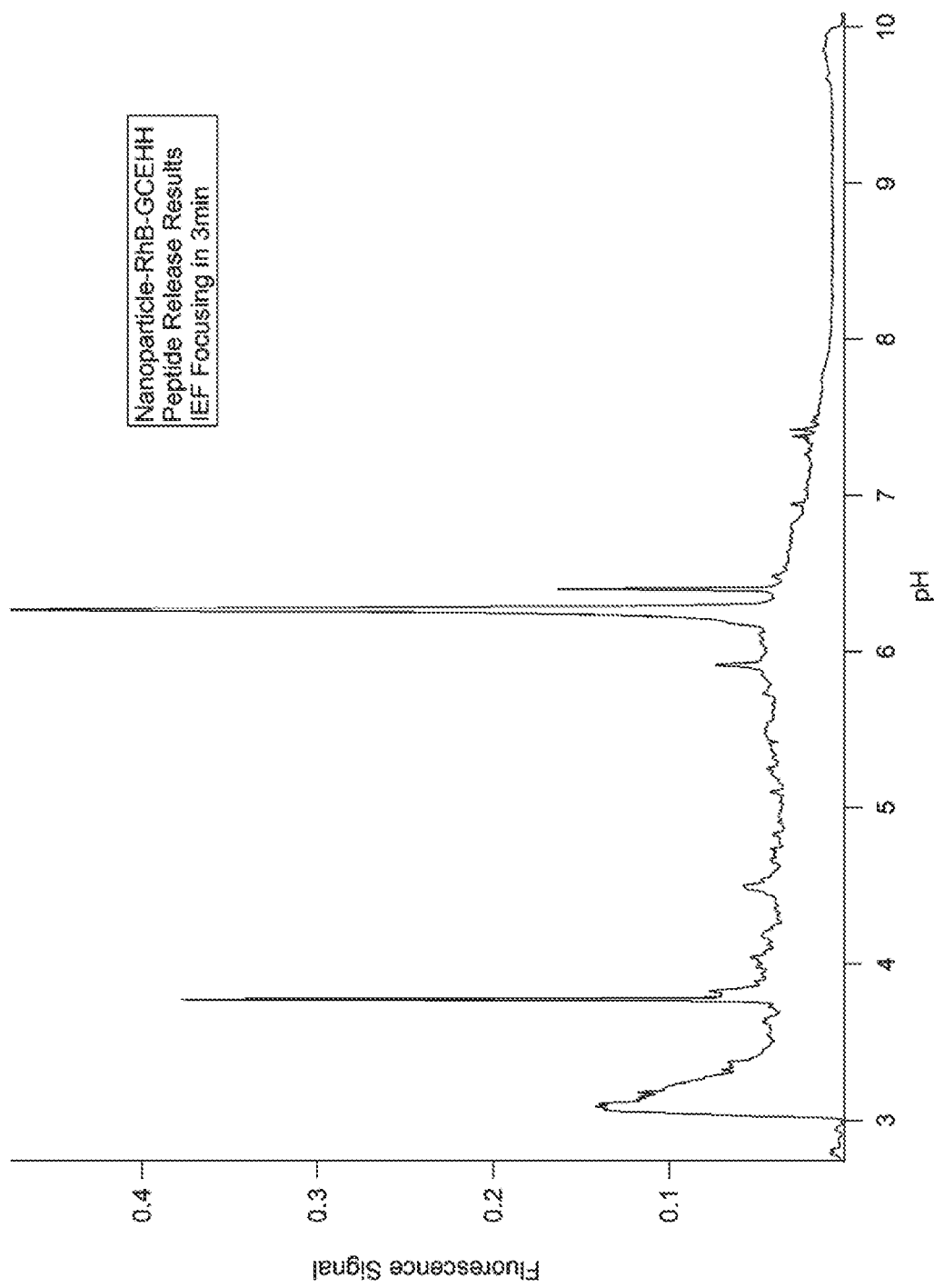
FIG. 9 is a graph showing isoelectric focusing results following disulfide reduction.

In a first disulfide reduction test (results shown in FIG. 8), peptide (RhB-GCYYKK, SEQ ID NO: 107) was attached via disulfide bond to cysteine coated 5 nm nanoparticles with a dopamine coating to reduce aggregation. In a second disulfide reduction test (results shown in FIG. 9), Peptide (RhB-GCEHH, SEQ ID NO:108) was attached via disulfide bond to cysteine coated 35 nm $Fe/Fe_3O_4$ nanoparticles with a 3,4-diphenylacetic acid coating to reduce aggregation.

The invention claimed is:

1. A method of microfluidic detection of a target analyte in a biological sample collected from a subject, the method comprising:
  providing a microfluidic device, said device comprising:
    a planar substrate comprising a sample inlet well positioned above a sample chamber in or on the substrate and a detection chamber in fluid communication with the sample chamber via a microfluidic channel extending from the sample chamber to the detection chamber; and a washing chamber positioned along the microfluidic channel intermediate to the sample chamber and the detection chamber; and
    a magnet positioned external and adjacent to said microfluidic channel, wherein said magnet is translatable along a plane parallel and to the plane of said microfluidic channel;
  incubating said biological sample with a first nanobiosensor in said sample chamber, wherein said first nanobiosensor comprises a magnetic nanoparticle releasably attached to a plurality of reporter molecules;
  transferring said incubated sample and said first nanobiosensor to said wash chamber;
  introducing a wash fluid into said wash chamber to yield a first washed nanobiosensor;
  magnetically transferring said first washed nanobiosensor to said detection chamber by translating said magnet along a plane parallel to said microfluidic channel from a position adjacent said wash chamber to a position adjacent said detection chamber;
  separating said nanoparticle and said reporter molecules to yield separated reporter molecules and a delinked nanoparticle,
  magnetically removing said delinked nanoparticle from said detection chamber by translating said magnet along a plane parallel to said microfluidic channel away from said detection chamber;
  detecting said separated reporter molecules in said detection chamber by microfluidic Isoelectric Focusing of said separated reporter molecules and detecting locations of said separated reporter molecules in said detection chamber, wherein said reporter molecules are indicative of interaction of said target analyte with said reporter molecules.

2. The method of claim 1, wherein said magnetic nanoparticle is releasably attached to a plurality of said reporter molecules via respective release units, wherein said release units are selected from the group consisting of reducible disulfide bridge, pH-sensitive linkage, photosensitive linkage, and thermosensitive linkages.

3. The method of claim 1, wherein said magnetic nanoparticle comprises any type of ferromagnetic metal (including elemental metal) or metal alloy selected from the group consisting of iron (Fe), nickel (Ni), cobalt (Co), certain alloys of rare-earth metals, and the oxides, hydroxides, sulfides, selenides, and tellurides of the foregoing, and combinations thereof.

4. The method of claim 1, wherein said magnetic nanoparticle is a core/shell nanoparticle selected from the group consisting of Fe/Au, Fe(0)/Fe$_3$O$_4$, and Au/Fe$_2$O$_3$.

5. The method of claim 1, wherein said reporter molecules are peptide sequences comprising a target analyte recognition sequence, detectable label, and one or more optional pI tag(s).

6. The method of claim 5, wherein said recognition sequence is selected from the group consisting of a supramolecular recognition sequence, a protease consensus sequence, and a post-translationally modifiable sequence.

7. The method of claim 5, wherein said detecting comprises exposing said detection chamber to an energy source to generate a detectable signal from said detectable label.

8. The method of claim 1, wherein said incubating comprises mixing said biological sample and said nanobiosensor by rotating said magnet in a position adjacent to said sample chamber, thereby magnetically moving said nanobiosensors throughout said biological sample.

9. The method of claim 1, wherein said magnet is positioned on a translatable stage below said microfluidic channel.

10. The method of claim 1, wherein said microfluidic channel further comprises one or more valves to provide forward and/or back pressure in said channel.

11. The method of claim 1, further comprising removing a portion of said biological sample via a waste outlet prior to magnetically transferring said first washed nanobiosensor to said detection chamber.

12. The method of claim 11, wherein said first nanobiosensor is present in said biological sample in a first concentration in said sample chamber; and wherein said washed nanobiosensor is present in a second concentration in said detection chamber, wherein said second concentration is greater than said first concentration.

13. The method of claim 1, wherein said detection chamber further comprises one or more inlets for applying an electrical current into said detection chamber.

14. The method of claim 1, further comprising incubating a plurality of additional nanobiosensors with said biological sample and first nanobiosensor in said sample chamber, wherein said plurality of additional nanobiosensors each comprise respective reporter molecules, wherein said respective reporter molecules are specific for a different target analyte than said first nanobiosensor.

15. The method of claim 14, wherein said separated reporter molecules are configured in a linearly spaced array of reporter molecules at respective locations in said detection chamber.

16. The method of claim 15, further comprising exposing said array to a light source and optically detecting the configuration of said array.

17. The method of claim 16, further comprising detecting the intensity of a detectable signal from said separated reporter molecules.

* * * * *